(12) United States Patent
Ehrenkranz et al.

(10) Patent No.: US 10,054,584 B2
(45) Date of Patent: Aug. 21, 2018

(54) DEVICE AND METHOD FOR PERFORMING A DIAGNOSTIC TEST

(71) Applicants: Joel R. L. Ehrenkranz, Salt Lake City, UT (US); Pamela J. Turbeville, Scottsdale, AZ (US); Jeong-Yeol Yoon, Tucson, AZ (US); David J. You, Tucson, AZ (US)

(72) Inventors: Joel R. L. Ehrenkranz, Salt Lake City, UT (US); Pamela J. Turbeville, Scottsdale, AZ (US); Jeong-Yeol Yoon, Tucson, AZ (US); David J. You, Tucson, AZ (US)

(73) Assignee: I-CALQ, LLC, Salt Lake City, UT (US)

( * ) Notice: Subject to any disclaimer, the term of this patent is extended or adjusted under 35 U.S.C. 154(b) by 639 days.

(21) Appl. No.: 14/070,276

(22) Filed: Nov. 1, 2013

(65) Prior Publication Data
US 2014/0213468 A1    Jul. 31, 2014

Related U.S. Application Data

(63) Continuation of application No. 13/612,293, filed on Sep. 12, 2012, now Pat. No. 8,889,424.
(Continued)

(51) Int. Cl.
*B01L 3/00* (2006.01)
*G01N 33/53* (2006.01)
(Continued)

(52) U.S. Cl.
CPC ......... *G01N 33/5302* (2013.01); *G01N 21/49* (2013.01); *G01N 33/558* (2013.01);
(Continued)

(58) Field of Classification Search
CPC ............. G01N 33/558; G01N 21/8483; G01N 33/54313; G01N 21/49; G01N 33/50;
(Continued)

(56) References Cited

U.S. PATENT DOCUMENTS

| | | | |
|---|---|---|---|
| 9,096,892 B1* | 8/2015 | Klemer | C12Q 1/6827 |
| 2004/0232052 A1* | 11/2004 | Call | B01D 21/2455 |
| | | | 209/143 |

(Continued)

OTHER PUBLICATIONS

Posthuma-Trumpie et al. ("Lateral flow (immuno)assay: its strengths, weaknesses, opportunities and threats. A literature survey" Anal Bioanal Chem (2009) 393:569-582 DOI 10.1007/s00216-008-2287-2).*
(Continued)

*Primary Examiner* — Erik B Crawford
(74) *Attorney, Agent, or Firm* — Magleby Cataxinos & Greenwood, PC

(57) ABSTRACT

Devices and methods for performing a point of care diagnostic test for detecting and quantifying at least one analyte in a biological sample. The device may include an immunoassay apparatus and a holder with a variable angle stage for positioning the immunoassay apparatus relative to a light source and a detector device. In one embodiment, the device is based upon elastic light scattering, so the variation in the angle of incidence and angle of reflection are optimized to maximize signal generation due to elastic light scattering. The detector device may include a wired or wireless connection to a computer network for communicating with an electronic medical records system, uploading the amount or concentration of at least one analyte present in the sample to the electronic medical records system, or querying a decision support algorithm stored in a computer readable format. The detector device may further include an onboard interpretive algorithm.

13 Claims, 13 Drawing Sheets

Related U.S. Application Data

(60) Provisional application No. 61/533,959, filed on Sep. 13, 2011.

(51) Int. Cl.
*G01N 21/49* (2006.01)
*G01N 33/558* (2006.01)
*G01N 33/78* (2006.01)

(52) U.S. Cl.
CPC .......... *G01N 33/78* (2013.01); *Y10S 435/805* (2013.01); *Y10S 435/97* (2013.01); *Y10S 436/81* (2013.01)

(58) Field of Classification Search
CPC .......... G01N 33/5302; G01N 15/1463; G01N 2015/1486; G01N 2021/6439; G01N 2035/00108; G01N 21/17; G01N 21/6428; G01N 21/78
See application file for complete search history.

(56) References Cited

U.S. PATENT DOCUMENTS

| | | | | |
|---|---|---|---|---|
| 2006/0222567 A1* | 10/2006 | Kloepfer | ............... | G01N 21/78 422/68.1 |
| 2010/0136521 A1* | 6/2010 | Yoon | .................... | G01N 33/569 435/5 |
| 2010/0254581 A1* | 10/2010 | Neeser | ................. | A61B 5/0077 382/128 |
| 2010/0297659 A1* | 11/2010 | Yoo | .................. | G01N 35/00029 435/6.16 |
| 2012/0123686 A1* | 5/2012 | Xiang | ................. | G06F 19/3406 702/19 |
| 2012/0226117 A1* | 9/2012 | Lamego | ............. | A61B 5/14532 600/316 |

OTHER PUBLICATIONS

You et al. (Direct and sensitive detection of foodborne pathogens within flesh produce samples using a field-deployable handheld device, Biosensors and Bioelectronics 28: 399-406 (Aug. 2011 online)).*

Smith ZJ, Chu K, Espenson AR, Rahimzadeh M, Gryshuk A, et al. (2011) Cell-Phone-Based Platform for Biomedical Device Development and Education Applications. PLoS One 6(3): e17150. doi:10.1371/journal.pone.0017150.*

\* cited by examiner

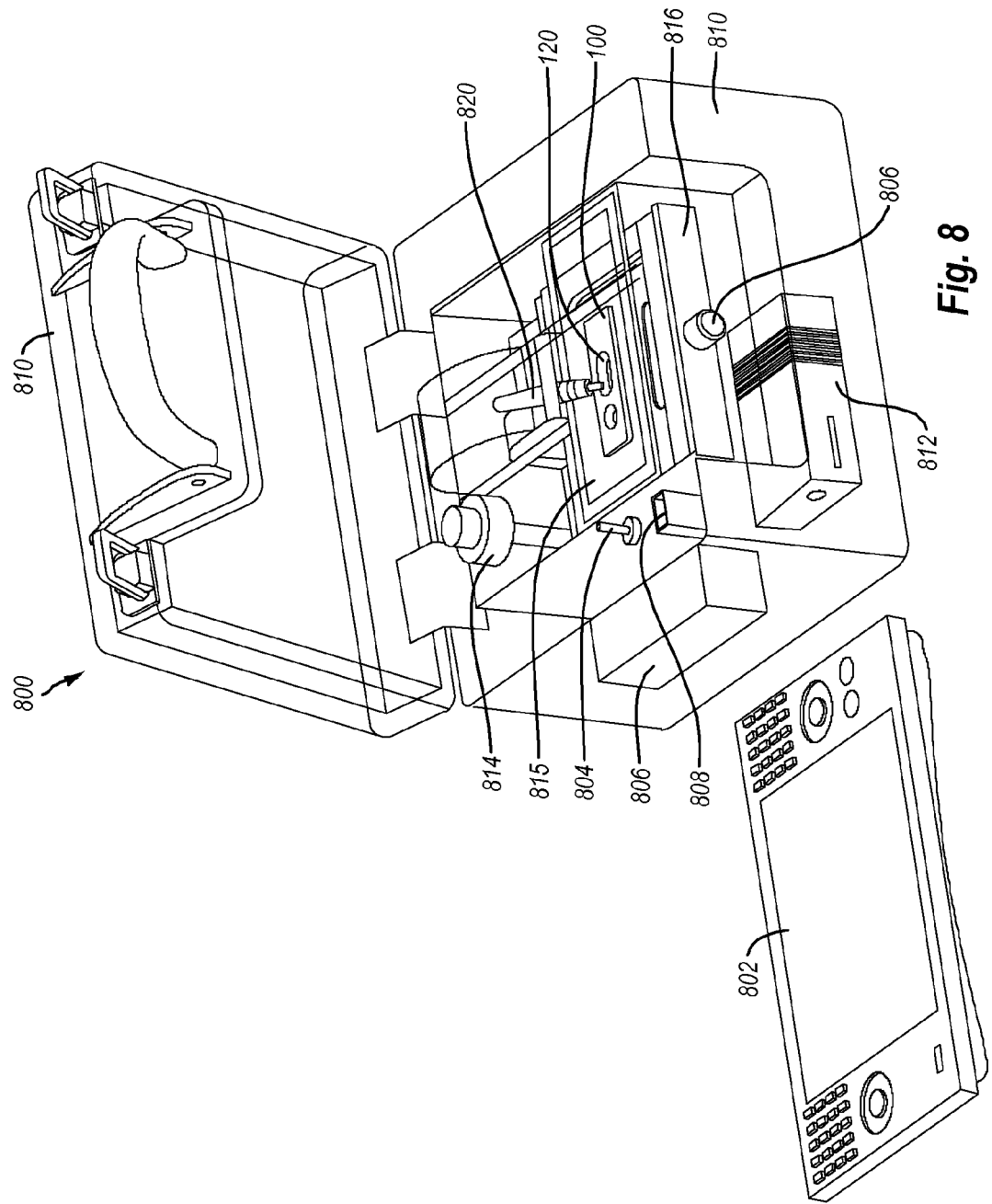

DEVICE AND METHOD FOR PERFORMING A DIAGNOSTIC TEST

CROSS-REFERENCE TO RELATED APPLICATIONS

The application is a continuation of, and claims the benefit of U.S. Non-prov. patent application Ser. No. 13/612,293 filed 12 Sep. 2012, which claims the benefit of and priority to U.S. Prov. Pat. App. Ser. No. 61/533,959 filed 13 Sep. 2011 and entitled "DEVICE AND METHOD FOR PERFORMING A DIAGNOSTIC TEST," each of which is incorporated by reference in its entirety.

BACKGROUND

Sampling and testing of biological samples and body fluids (e.g., saliva, blood, urine, fecal matter, foods, plants, fish, minerals, animals, etc) is common for both testing and monitoring humans, fish, animals, and plants for any number of biochemical or physiological conditions and, of course, for determining the general state of health of an organism. For example, sampling and testing of human body fluids is often performed for point-of-care testing ("POCT"). POCT is defined as medical testing at or near the site of patient care. The driving notion behind POCT is to bring the test conveniently and immediately to the patient. This increases the likelihood that the patient, physician, and care team will receive the results more quickly, which allows for immediate clinical management decisions to be made. POCT examples include, but are not limited to, blood glucose testing, hormone testing, cardiac pulmonary, gastroenterology, urology, dermatology, neurology, pediatrics, surgical, public health, bioterrorism, food safety, and veterinary and plant pathology testing, metabolic testing (e.g., thyroid stimulating hormone), blood gas and electrolytes analysis, rapid coagulation testing, rapid cardiac markers diagnostics, drugs of abuse screening, urine testing, pregnancy testing, fecal occult blood analysis, food pathogen screening, complete blood count ("CBC"), hemoglobin diagnostics, infectious disease testing, cholesterol screening cancer testing (e.g. PSA), hormone testing (hCG, LH, FSH), cardiac (troponin), pulmonary, gastroenterology (e.g., *H. pylori* antibodies), urology, dermatology, neurology, pediatrics, surgical, and public health (Ebola, cholera, HIV), and combinations thereof.

One testing method that is often employed for POCT and more conventional testing involves the use of lateral-flow chromatographic immunoassay cassettes. Lateral-flow chromatographic immunoassay cassettes can be used to easily and quickly obtain a variety of qualitative results relating to a number of biochemical and physiological conditions and disease states of an individual. These kinds of tests require the end user to simply add a sample to the cassette and then observe the result a few minutes later. Since such rapid and easy-to-use tests are user friendly, they are very popular in both the professional and consumer markets nowadays. Such tests are also very popular in areas where access to trained health care professionals is limited or where access to proper medical facilities is limited (e.g., poor areas, developing countries, war zones, etc).

Lateral flow chromatographic immunoassay methods and devices have been described extensively. See, e.g., Gordon and Pugh, U.S. Pat. No. 4,956,302; H. Buck, et al., WO 90/06511; T. Wang, U.S. Pat. No. 6,764,825; W. Brown, et al., U.S. Pat. No. 5,008,080; Kuo and Meritt, U.S. Pat. No. 6,183,972, EP 00987551A3. Such assays involve the detection and determination of an analyte substance that is a member of a specific binding pair consisting of a ligand and a receptor. The ligand and the receptor are related in that the receptor specifically binds to the ligand, being capable of distinguishing a specific ligand or ligands from other sample constituents having similar characteristics. Immunological assays involving reactions between antibodies and antigens are one such example of a specific binding assay. Other examples include DNA and RNA hybridization reactions and binding reactions involving hormones and other biological receptors. One well-known commercial embodiment of this technique is the Clearblue One-Step Pregnancy Test.

Lateral flow chromatographic immunoassay test cassettes have a number of desirable characteristics including their ease of use and broad applicability to a variety of analytes. Likewise, immunoassay procedures capable of being carried out on a test strip and which can be administered in the field or other locations where medical testing laboratories are not readily available have provided a great benefit to the diagnosis and control of disease. Currently, however, such lateral flow chromatographic immunoassay tests are generally only capable of providing qualitative results. That is, while currently available lateral flow chromatographic immunoassay test cassettes and cassette reader apparatuses are particularly well-suited for telling a practitioner whether or not one or more test substances are present in a sample above a given detection limit, they are poorly suited for providing quantitative results. There is an ongoing need in the art for devices and methods that combine the ease of use characteristics of lateral flow chromatographic immunoassay tests with systems that are designed to provide quantitative results. Such devices and methods may, for example, allow medical practitioners to diagnose a variety of conditions at the point of care (e.g., chair-side or essentially anywhere in the world) without being tied to a medical facility or a testing laboratory.

BRIEF SUMMARY

A device and method for performing a point of care diagnostic test for detecting and quantifying at least one analyte in a biological sample (e.g., a body fluid). In one embodiment, the device disclosed herein may include an immunoassay apparatus (i.e., a lateral flow immunochromatographic assay cassette) and a sample holder with an adjustable variable angle stage for positioning the immunoassay apparatus relative to a light source and a detector device to optimize elastic light scattering. In another embodiment, the device includes an interface for a light source (e.g., an optical fiber or light pipe), an interface (e.g., a collimating lens) for a external digital imager (e.g CCD or CMOS chip), and an adjustable variable angle stage that positions a lateral flow immunochromatographic assay cassette so as to optimize the angle of incidence and angle of radiation to optimize an elastic light scattering signal from the a lateral flow immunochromatographic assay cassette. The device is based upon elastic light scattering, so the variation in the angle of incidence and angle of reflection are optimized to maximize signal generation due to elastic light scattering. In one embodiment, the device disclosed herein may include an immunoassay apparatus, a detector device (e.g., a digital camera) positioned to capture at least one image of a visual signal output of the immunoassay apparatus, a light source positioned to illuminate the immunoassay apparatus with at least one wavelength of light selected to interact with the visual signal output produced by the immunoassay apparatus, and a holder configured to couple the immunoassay apparatus to the detector device in proximity to the light source.

In one embodiment, the first angle between the light source (i.e., incident light) and the immunoassay apparatus, and the second angle between the detector device and the immunoassay apparatus (i.e., elastically scattered light) is adjustable to improve at least one of a signal-to-noise ratio or a detection limit for the at least one analyte. Optimizing these two angles enables the user to maximize the elastic light scattering signal from the immunoassay apparatus while minimizing the non-specific light from the apparatus. In one embodiment, the first angle between the light source (i.e., incident light) and the immunoassay apparatus, and the second angle between the detector device (e.g., scattered, emitted, or reflected light) and the immunoassay apparatus is adjustable to improve at least one of a signal-to-noise ratio or a detection limit for the at least one analyte. Optimizing these two angles enables the user to maximize the scattered, emitted, or reflected (i.e., specific) light from the immunoassay apparatus while minimizing the non-specific light from the apparatus.

In one embodiment, a single immunoassay device may contain multiple types of different antibodies each conjugated with different dyes (e.g., quantum dots) and multiple capture bands each immobilized with different antibodies. A single light source (e.g., ultraviolet light) illuminates all dyes (e.g., quantum dots) simultaneously, and the detector device (e.g., a miniature spectrophotometer or a digital camera) captures the emitted signals from multiple bands simultaneously.

In one embodiment, the detector device further includes or can remotely access an interpretive algorithm that is adapted for interpreting and/or aiding interpretation of the results of the immunoassay. The interpretive algorithm may include one or more computer storage media having stored thereon computer executable instructions that, when executed by one or more processors (of the detector device), implement a method for interpreting a numerical value related to the visual signal output produced by the immunoassay apparatus in response to the presence or amount of the at least one analyte present in the sample. In one embodiment, the computer implemented method includes (1) receiving a user initiated request to convert the visual signal readout of the immunoassay apparatus to a numerical value, (2) in response to the request, an act of identifying at least one elastic light scattering signal of the immunoassay apparatus, (3) capturing at least one elastic light scattering signal from the immunoassay apparatus, (4) converting the one elastic light scattering signal to at least one numerical value proportional at least one of an intensity or density of the elastic light scattering signal, and (5) using the at least one numerical value to determine an amount or concentration of at least one analyte present in the sample. This numerical value can then be displayed on a screen located on the detector device and/or stored, interpreted, or sent to a database. In one embodiment, the computer implemented method includes (1) receiving a user initiated request to convert the visual signal readout of the immunoassay apparatus to a numerical value, (2) in response to the request, an act of identifying at least one visual signal readout of the immunoassay apparatus, (3) capturing at least one digital photographic image of the at least one visual signal readout of the immunoassay apparatus, (4) converting the at least digital photographic image to at least one numerical value proportional at least one of an intensity, a density, or a number of pixels in the at least one digital photographic image of the at least one visual signal readout of the immunoassay apparatus, and (5) using the at least one numerical value to determine an amount or concentration of at least one analyte present in the sample. This numerical value can then be displayed on a screen located on the detector device and/or stored, interpreted, or sent to a database.

In another embodiment, a method for detecting at least one analyte of interest in a sample is disclosed. The method includes (1) providing a lateral-flow chromatographic immunoassay cassette that includes at least one ligand immobilized thereon, wherein the at least one ligand is capable of capturing an analyte of interest on the lateral-flow chromatographic immunoassay cassette (2) applying a liquid sample to the lateral-flow chromatographic immunoassay cassette, wherein the sample includes at least one analyte of interest, (3) coupling the lateral-flow chromatographic assay cassette to a sample holder configured to angle the lateral-flow chromatographic assay cassette in relation to a detector device, and (4) observing the presence of the at least one analyte of interest by elastic light scattering. In one embodiment, the device includes an illumination source, a miniature spectrophotometer, at least one optical fiber capable of transmitting an illuminating light from the illumination source to the lateral-flow chromatographic assay cassette, a collimating lens capable of transmitting a signal from the lateral-flow chromatographic assay cassette to the miniature spectrophotometer, and an adjustable variable angle stage configured for holding the lateral-flow chromatographic assay cassette at an angle greater than or less than zero degrees in relation to the illuminating light and the miniature spectrophotometer, wherein the illuminating light and the and the miniature spectrophotometer are positioned to illuminate at least a portion of the lateral-flow chromatographic assay cassette and optimize an elastic light scattering signal from the lateral-flow chromatographic assay cassette. In another embodiment, a method for detecting at least one analyte of interest in a sample is disclosed. The method includes (1) providing a lateral-flow chromatographic immunoassay cassette that includes at least one ligand immobilized thereon, (2) applying a liquid sample to the lateral-flow chromatographic immunoassay cassette, wherein the sample includes at least one analyte of interest, (3) observing an interaction of the at least one analyte of interest with the at least one ligand immobilized on the lateral-flow chromatographic immunoassay cassette with a device that includes a digital camera device, a light source, and a holder configured to couple the lateral-flow chromatographic immunoassay cassette to the digital camera device in proximity to the light source. The holder is adjustable to adjust the angle of the immunoassay apparatus relative to the light source and the digital camera device to improve at least one of a signal-to-noise ratio or a detection limit for the at least one analyte of interest. The method further includes (4) querying an interpretive algorithm stored in a computer readable format in the digital camera device to convert the observed interaction of the at least one analyte of interest with the at least one ligand visual readout to a numerical value related to the presence or amount of the at least one analyte of interest present in the sample.

In another embodiment, the present invention provides:

1. A system, comprising: an assay apparatus configured for providing a signal in response to at least one analyte of interest in a sample; a detector device; a light source configured to transmit at least one wavelength of light capable of interacting with the signal of the assay apparatus; and a holder configured to couple the assay apparatus to the detector device in proximity to the light source, wherein the light source is positioned to illuminate at least a portion of the assay apparatus and the detector is positioned to capture at least one image of the illuminated signal.

2. The system of claim 1, further comprising an interpretive algorithm stored in a computer readable format and electronically coupled to the detector device, wherein the interpretive algorithm is configured to convert the at least one image of the illuminated signal to a numerical value related to the presence or amount of the at least one analyte present in a sample.

3. The diagnostic testing system of claim 1, wherein the assay apparatus is a lateral-flow chromatographic assay cassette having at least one ligand immobilized thereon configured for capturing an analyte of interest.

4. The system of claim 4, wherein the holder includes an electrical connector configured to draw power from the detector device to power the light source.

5. The system of claim 1, wherein the detector device is a digital camera device.

6. The system of claim 3, wherein the digital camera device is one of a camera phone or a compact digital camera.

7. The system of claim 3, wherein the light source is one of a flash or autofocus illuminator included on the digital camera device.

8. The system of claim 1, wherein at least one wavelength filter is interposed between the light source and the assay apparatus.

9. The system of claim 1, wherein the light source includes at least one of a camera flash, an autofocus illuminator, ambient light, sunlight, an LED light, an incandescent lamp, or a gas-discharge lamp.

10. The method of claim 1, wherein the light source is configured to yield at least one wavelength of light selected to convert the signal of the assay apparatus to a fluorescent emission signal.

11. The system of claim 1, wherein the light source includes at least one focusing apparatus for focusing the light source on the assay apparatus.

12. The system of claim 1, wherein the assay apparatus includes a lateral-flow chromatographic assay cassette.

13. The system of claim 10, wherein the a lateral-flow chromatographic assay cassette comprises: a base; a strip positioned above the base including a wicking material, wherein the strip includes a distal end and a proximal end; and a sample application zone positioned between the distal end and the proximal end, wherein a liquid sample applied to the sample application zone diffuses through the absorbent strip from the distal end to the proximal end, and wherein an analyte of interest, if present in the sample, interacts with at least a first antibody immobilized in the absorbent strip to yield a signal that can be detected by the detector device.

14. The system of claim 1, wherein the holder is configured to adjust the angle of the assay apparatus relative to the light source and the detector device.

15. The system of claim 1, wherein the holder is configured to adjust the angle of the assay apparatus relative to the light source and the detector device to improve at least one of a signal-to-noise ratio or a detection limit.

16. The system of claim 1, wherein the holder includes a device for automatically sampling a number of angles of the assay apparatus relative to the light source and the detector device to improve at least one of a signal-to-noise ratio or a detection limit.

17. A diagnostic testing system, comprising: a lateral-flow chromatographic assay cassette that includes at least one ligand immobilized thereon configured to interact with at least one analyte present in a sample to provide a visual readout related to the presence or amount of the at least one analyte present in the sample; a digital camera device; a light source capable of producing light having at least one wavelength or a range of wavelengths selected to illuminate the visual readout of the lateral-flow chromatographic assay cassette; a holder configured to couple the lateral-flow chromatographic assay cassette to the digital camera device in proximity to the light source, wherein the holder is adjustable to position the light source to illuminate at least a portion of the lateral-flow chromatographic assay cassette and the camera is positioned to capture at least one image of the visual readout; and an interpretive algorithm stored in a computer readable format in the digital camera device, wherein the interpretive algorithm is configured to convert the visual readout to a numerical value related to the presence or amount of the at least one analyte present in a sample.

18. The diagnostic testing system of claim 17, wherein the digital camera device is one of a camera phone or a compact digital camera.

19. The diagnostic testing system of claim 17, wherein the sample is selected from the group consisting of a saliva sample, a blood sample, a blood extract, a urine sample, a fecal matter sample, a pathology sample, a plant material, a food sample, and combinations thereof.

20. The diagnostic testing system of claim 17, wherein the sample includes at least one control substance and at least one test substance.

21. The diagnostic testing system of claim 20, wherein the positive control substance is detectable at least one of a different time than the at least one test substance at a wavelength different than the wavelength used to detect the at least one test substance.

22. The diagnostic testing system of claim 20, wherein the positive control substance migrates through the lateral-flow chromatographic assay cassette at different rate than the at least one test substance.

23. The diagnostic testing system of claim 20, wherein the at least one test substance includes blood glucose, thyroid stimulating hormone, blood gas and electrolytes analysis, cardiac markers, drugs of abuse, a urine component, a pregnancy hormone marker, fecal occult blood, a food pathogen, complete blood count ("CBC"), cholesterol, a cancer marker, a hormone, an antibody associated with a pathogen, a pathogen, and combinations thereof.

24. The diagnostic testing system of claim 20, wherein a limit of detection for the at least one test substance is within a clinically accepted range.

25. The diagnostic testing system of claim 24, wherein the limit of detection is a function of at least one of an angle between the digital camera device and the light source, an angle between the lateral-flow chromatographic assay cassette and the light RI source, or an angle between the digital camera device and the lateral-flow chromatographic assay cassette.

26. The diagnostic testing system of claim 17, wherein the interpretive algorithm includes one or more computer storage media having stored thereon computer executable instructions that, when executed by one or more processors of the digital camera device, implement a method for interpreting the numerical value related to the presence or amount of the at least one analyte present in the sample, the method comprising: receiving a user initiated request to the visual readout of the lateral-flow chromatographic assay cassette to a numerical value; in response to the request, an act of identifying at least one visual readout of the lateral-flow chromatographic assay cassette; capturing at least one digital photographic image of the at least one visual readout of the lateral-flow chromatographic assay cassette; converting the at least digital photographic image to at least one numerical value proportional to at least one of an intensity, a density, or a number of pixels in the at least one digital photographic image of the at least one visual readout of the lateral-flow chromatographic assay cassette; and using the at least one numerical value to determine an amount or concentration of at least one analyte present in the sample.

27. The diagnostic testing system of claim 26, the computer implemented method further including at least one of: communicating with an electronic medical records system via a wireless communication channel; uploading the amount or concentration of the at least one analyte present in the sample to the electronic medical records system; querying a decision support algorithm, wherein the decision support algorithm uses the at least one numerical value to support a diagnosis of at least one condition in a subject and to suggest a course of treatment.

28. A method for detecting at least one analyte of interest in a sample, the method comprising: providing a lateral-flow chromatographic assay cassette that includes at least one ligand immobilized thereon; applying a liquid sample to the lateral-flow chromatographic assay cassette, wherein the sample includes at least one analyte of interest; observing an interaction of the at least one analyte of interest with the at least one ligand immobilized on the lateral-flow chromatographic assay cassette with a device that includes a digital camera device, a light source, and a holder configured to couple the lateral-flow chromatographic assay cassette to the digital camera device in proximity to the light source, wherein the holder is adjustable to adjust the angle of the assay apparatus relative to the light source and the digital camera device to improve at least one of a signal-to-noise ratio or a detection limit for the at least one analyte of interest; and querying an interpretive algorithm stored in a computer readable format in the digital camera device to convert the observed interaction of the at least one analyte of interest with the at least one ligand visual readout to a numerical value related to the presence or amount of the at least one analyte of interest present in the sample.

29. The method of claim 28, wherein the ligand includes at least one of an antibody, an epitope, or a nucleic acid immobilized on the lateral-flow chromatographic assay cassette.

30. The method of claim 28, further comprising mixing the liquid sample with a dye conjugate prior to applying the sample to the lateral-flow chromatographic assay cassette.

31. The method of claim 30, wherein the dye conjugate is configured to interact with at least one of the analyte of interest or the ligand to provide a visual readout related to the presence or concentration of the analyte of interest in the sample.

32. The method of claim 28, further comprising sampling a number of angles relative to the lateral-flow chromatographic assay cassette, the light source, and the digital camera device to improve at least one of the signal-to-noise ratio or the detection limit for the at least one analyte of interest.

33. The method of claim 28, wherein the sample includes at least one control substance and at least one analyte of interest.

34. The method of claim 33, further comprising timing the observing of the interaction of the at least one analyte of interest with the at least one ligand immobilized on the lateral-flow chromatographic assay cassette by observing the at least one control substance.

35. The method of claim 34, further comprising observing the at least one analyte of interest when the at least one control substance appears.

36. The method of claim 28, wherein the interpretive algorithm includes one or more computer storage media having stored thereon computer executable instructions that, when executed by one or more processors of the digital camera device, implement a method for interpreting the numerical value related to the presence or amount of the at least one analyte present in the sample, the method comprising:

receiving a user initiated request to convert the observed interaction to a numerical value; in response to the request, an act of identifying at least one interaction of the at least one analyte of interest with the ligand immobilized on the lateral-flow chromatographic assay cassette; capturing at least one digital photographic image of the at least one interaction; converting the at least digital photographic image to at least one numerical value proportional to at least one of an intensity, a density, or a number of pixels associated with the at least one interaction; and using the at least one numerical value to determine an amount or concentration of at least one analyte present in the sample.

37. The method of claim 36, the computer implemented method further including at least one of: communicating with an electronic medical records system via a wireless communication channel; uploading the amount or concentration of the at least one analyte present in the sample to the electronic medical records system; querying a decision support algorithm, wherein the decision support algorithm uses the at least one numerical value to support a diagnosis of at least one condition in a subject and to suggest a course of further evaluation and/or treatment.

38. The method of claim 37, wherein the decision support algorithm is stored in a computer readable format in one or more computer storage media on the digital camera device.

39. The method of claim 37, wherein the decision support algorithm is stored in a computer readable format on a remote database.

40. The method of claim 3, wherein the ligand is one of an antibody, an epitope, a nucleic acid, and combinations thereof.

These and other objects and features of the present invention will become more fully apparent from the following description and appended claims, or may be learned by the practice of the invention as set forth hereinafter.

BRIEF DESCRIPTION OF THE DRAWINGS

To further clarify the above and other advantages and features of the present invention, a more particular description of the invention will be rendered by reference to specific embodiments thereof which are illustrated in the appended drawings. It is RI appreciated that these drawings depict only illustrated embodiments of the invention and are therefore not to be considered limiting of its scope. The invention will be described and explained with additional specificity and detail through the use of the accompanying drawings in which:

FIG. 8 illustrates an alternative embodiment of a diagnostic testing system that includes a lateral-flow chromatographic immunoassay cassette, a miniature spectrophotometer, a stage holding the lateral-flow chromatographic immunoassay cassette, an angularly adjustable illumination/detection system, a power source, and a separate computing device.

DETAILED DESCRIPTION

A device and method for performing a point of care diagnostic test for detecting and quantifying at least one analyte in a biological sample (e.g., a body fluid). In one embodiment, the device disclosed herein may include an immunoassay apparatus (i.e., a lateral flow immunochromatographic assay cassette) and a holder with an adjustable variable angle stage for positioning the immunoassay apparatus relative to a light source and a detector device to optimize elastic light scattering. In another embodiment, the device includes an interface for a light source (e.g., an optical fiber or light pipe), an interface (e.g., a collimating lens) for a external digital imager (e.g CCD or CMOS chip), and an adjustable variable angle stage that positions a lateral flow immunochromatographic assay cassette so as to optimize the angle of incidence and angle of radiation to optimize an elastic light scattering signal from the a lateral flow immunochromatographic assay cassette. The device is based upon elastic light scattering, so the variation in the angle of incidence and angle of reflection are optimized to maximize signal generation due to elastic light scattering. In one embodiment, the device disclosed herein includes an immunoassay apparatus, a detector device (e.g., a digital camera) positioned to capture at least one image of a visual output signal of the immunoassay apparatus, a light source configured to transmit at least one wavelength of light capable of interacting with a visual signal readout produced on the immunoassay apparatus, and a holder configured to couple the immunoassay apparatus to the detector device in proximity to the light source. The angle between the light source (incident light) and the detector device (detected light) is adjustable to improve at least one of a signal-to-noise ratio or a detection limit. The detector device further includes or can remotely access an interpretive algorithm stored in a computer readable format.

Figure 1:
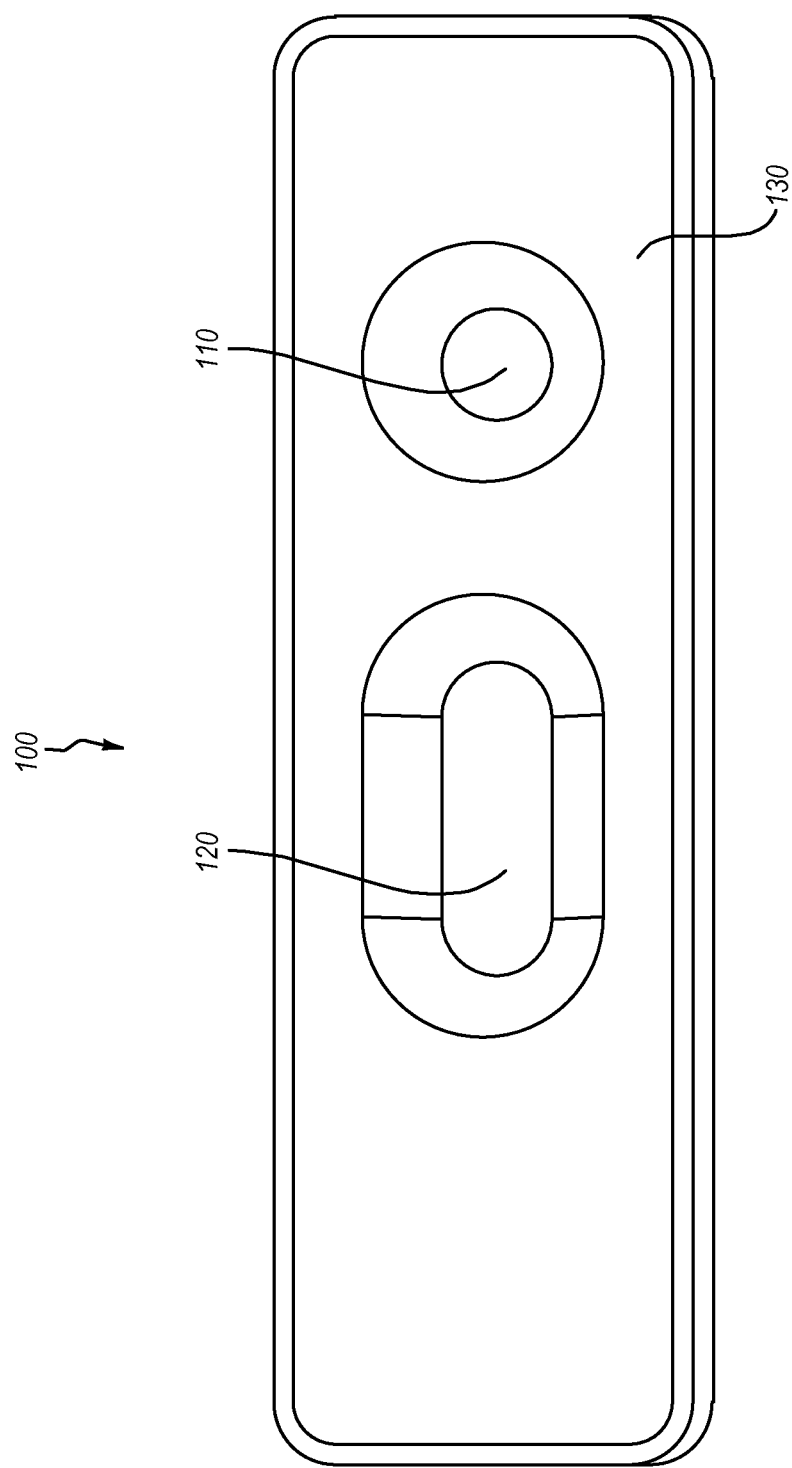
FIG. 1 illustrates a top view of a lateral-flow chromatographic immunoassay cassette.

I. Lateral-Flow Chromatographic Immunoassay Cassettes and Devices for Detecting and Interpreting Results of a Lateral-Flow Chromatographic Immunoassay Referring to FIG. 1, a typical lateral-flow chromatographic immunoassay cassette 100 is illustrated. The lateral-flow chromatographic immunoassay cassette 100 includes a plastic housing 130 containing a test strip, which is generally a plastic strip laminated with porous material that permits lateral flow of liquid. The illustrated lateral-flow chromatographic immunoassay cassette 100 includes a sample application zone 110 and an analysis zone 120.

In one type of lateral-flow chromatographic immunoassay cassette, the test strip is divided into four domains, which can be made of only one kind of material or several kinds of material (e.g., up to four different kinds of materials). The first domain is for sample addition. It functions to remove viscous and particulate materials in the sample and also to condition the sample solution for the reactions in the following domains. The second domain is a mobile-phase with a color conjugate. In one embodiment, the color conjugate may be made from conjugation between a visible color marker (e.g., colored beads, colloidal gold, fluorescent dyes, etc.) and a detection antibody. The detection antibody can bind a specific antigen in the sample (e.g., an analyte of interest or a positive control substance) and forms an antigen-color conjugate complex. The third domain of the lateral-flow chromatographic immunoassay cassette is a solid-phase with immobilized capture antibody. The capture antibody can bind the antigen of the antigen-color conjugate complex and forms capture antibody-antigen-color conjugate complex sandwich. The fourth domain is for solution absorption. It draws sample solution towards it continuously.

During the testing, sample added to the first domain flows to the second domain. If the antigen is present in the sample, it will bind the color conjugate to form antigen-color conjugate complex. This complex then migrates to the third domain to bind the capture antibody and forms the capture antibody-antigen-color conjugate complex sandwich. Since the capture antibody is immobilized in the third domain, the sandwich shows as a visible color signal or a fluorescent signal, depending on the dye type, on the site of the capture antibody. If there is no antigen in the sample, no sandwich can be formed and hence no visible color signal can be seen in the third domain. This is a so-called non-competitive immunoassay or a sandwich assay where the amount of signal is directly proportional to the concentration of the analyte of interest in the sample.

Lateral-flow chromatographic immunoassay cassettes can also be adapted for competitive immunoassays. In a competitive immunoassay, the analyte of interest in the unknown sample competes for binding to an antibody with a labeled analyte. In a competitive assay, the labeled analyte is able to provide a known signal. In the assay, the amount of labeled analyte bound to the antibody is measured and any reduction in the known signal is attributed to the presence of the analyte in the sample. That is, in this method, the response will be inversely related to the concentration of analyte in the unknown. This is because the greater the response, the less antigen in the unknown was available to compete with the labeled antigen.

Lateral-flow chromatographic immunoassay cassettes may be adapted for assaying a number of different analyte types. For example, immunoassay cassettes have been adapted or may in the future be adapted for blood glucose testing, metabolic testing (e.g., thyroid stimulating hormone), blood gas and electrolytes analysis, rapid coagulation testing, rapid cardiac markers diagnostics, drugs of abuse screening, urine testing, pregnancy testing, fecal occult blood analysis, food pathogen screening, complete blood count ("CBC"), hemoglobin diagnostics, infectious disease testing, cholesterol screening, hormone testing, cardiac pulmonary, gastroenterology, urology, dermatology, neurology, pediatrics, surgical, public health, and veterinary and plant pathology testing, combinations thereof, and the like.

Figure 2:
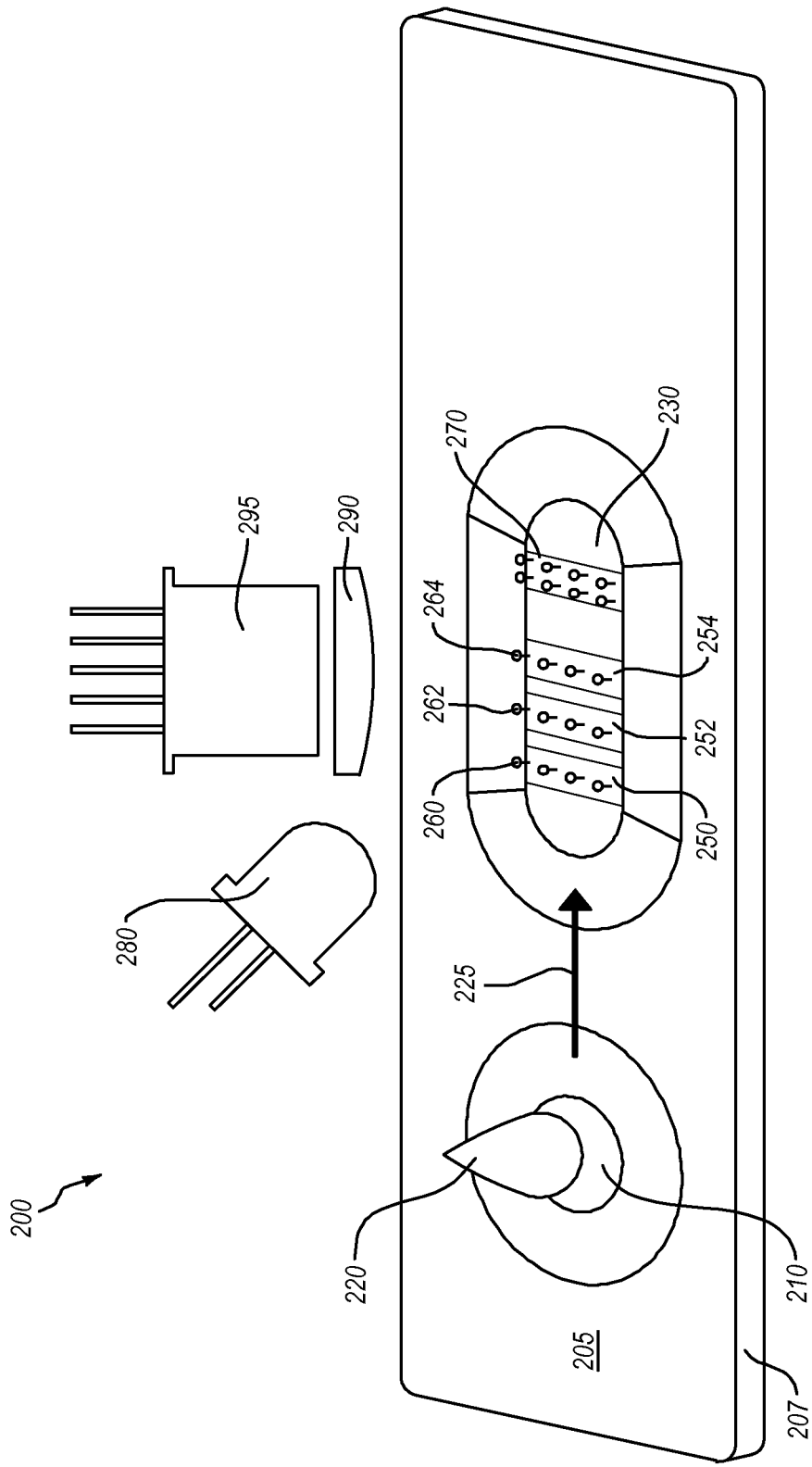
FIG. 2 illustrates the principles of multiplex detection in a single immunoassay cassette using multiple capture antibodies and multiple detection dyes (e.g., quantum dots)

Referring now to FIG. 2, a perspective view of a diagnostic test system 200 is illustrated. The diagnostic test system 200 includes a lateral-flow chromatographic assay cassette 205 and means for collecting assay data from the lateral-flow chromatographic assay cassette 205. Referring now to FIG. 2, a perspective view of a lateral-flow chromatographic immunoassay cassette that is configured for multiplex analysis is illustrated. In the embodiment illustrated in FIG. 2, the lateral-flow chromatographic immunoassay cassette includes multiple target antibody lines (e.g., 250—Target 1, 252—Target 2, and 254—Target 3) that are each configured to interact with a selected analyte of interest and a control line that is configured to provide a know readout. The analytes of interest can be detected on the various target lines with different colored dyes, and the like. In the illustrated embodiment, different colored quantum dots are associated with each of the target lines.

The lateral-flow chromatographic assay cassette 205 includes a plastic housing 207 containing a test strip, which is generally a plastic strip laminated with porous material that permits lateral flow of liquid. The illustrated lateral-flow chromatographic immunoassay cassette 205 includes a sample application zone 210 and an analysis zone 230.

When a sample 220 is applied to the lateral-flow chromatographic immunoassay cassette 205 at the sample application zone 210, the sample 220 diffuses through the strip in flow direction 225 toward the analysis zone 230. In the embodiment illustrated in FIG. 2, the analysis zone 230 includes a test line 240 that includes at least one capture ligand selected for capturing at least one analyte of interest in the sample 220. The analysis zone 230 further includes at least first and second calibration standard lines 250 and 254. Additionally, the analysis zone may include a positive control line 270 that may be configured to provide an indication regarding whether or not sample has diffused though the strip and whether or not the assay is functioning.

The analyte(s) of interest, the first and second calibration standards, and the positive control can be detected on their various target lines, 252, 250, 254 and 270, respectively, with various reporters. The reporters 260-264 for each of the various target lines, 252, 250, and 254 may be the same or different. Examples of suitable reporters include, but are not limited to, visible and fluorescent dyes, latex beads, enzymes, gold nanoparticles, silver nanoparticles, quantum dots, and the like. Quantum dots are nano-scale materials that can produce excited emission at particular wavelengths depending on their size and shape. Quantum dots can be used in immunoassays where dyes have traditionally been used. However, quantum dots are generally superior to traditional organic dyes on several counts: quantum dots are typically much brighter that organic dyes (owing to their high extinction coefficients combined with a comparable quantum yield to fluorescent dyes) as well as their stability (i.e., much less photobleaching). For example, it has been estimated that quantum dots are 20 times brighter and 100 times more stable than traditional fluorescent reporters.

Emission from the various reporters (e.g., quantum dots and other dyes) can be excited by a number of sources. In the illustrated embodiment, an LED light source 280 is used illuminate the analysis zone 230 of the lateral flow assay cassette 205. Illumination by the light source 280 may produce a detectable signal that includes at least one of emission (e.g., fluorescence), color, reflectance, diffuse scattering (i.e., scattering and absorbance), elastic light scattering, chemiluminescence, chemifluorescence, transmission, or absorbance from the reporters. A lens 290 (e.g., a collimating lens) and a detector (e.g., a CCD or CMOS camera) are used to collect data from the reporters and the first and second calibration standards. A collimating lens and a CCD camera are used to collect the emitted light. The intensity of each of the bands and the concentration of each of the analytes can be quantified as described in detail elsewhere herein.

When the sample 220 is applied to the diffusion strip of the lateral-flow chromatographic assay cassette 205, the liquid in the sample carries the analyte of interest through the diffusion strip in flow direction 225 into the analysis zone 230 where it can be captured by the capture ligand line 240. The first and second calibration standard lines 250 and 254 are selected to provide a detectable signal that correlate to non-zero concentration values of the analyte of interest. For example, the first and second calibration standard lines 250 and 254 may include an amount of the analyte of interest or another material pre-bound to the diffusion strip of the lateral-flow chromatographic assay cassette 205. The reporter 260 may be a diffusible material that can bind to the capture ligand line 250 and the first and second calibration standards 250 and 254 in an amount proportional to the amount of bound ligand is present in each line. In response to illumination by the light source, the reporter 260-264 bound to each of lines 250-254 provides a signal that can be used to calculate a calibration curves and, in turn, determine the concentration of the analyte of interest in the sample 220.

Figure 3:
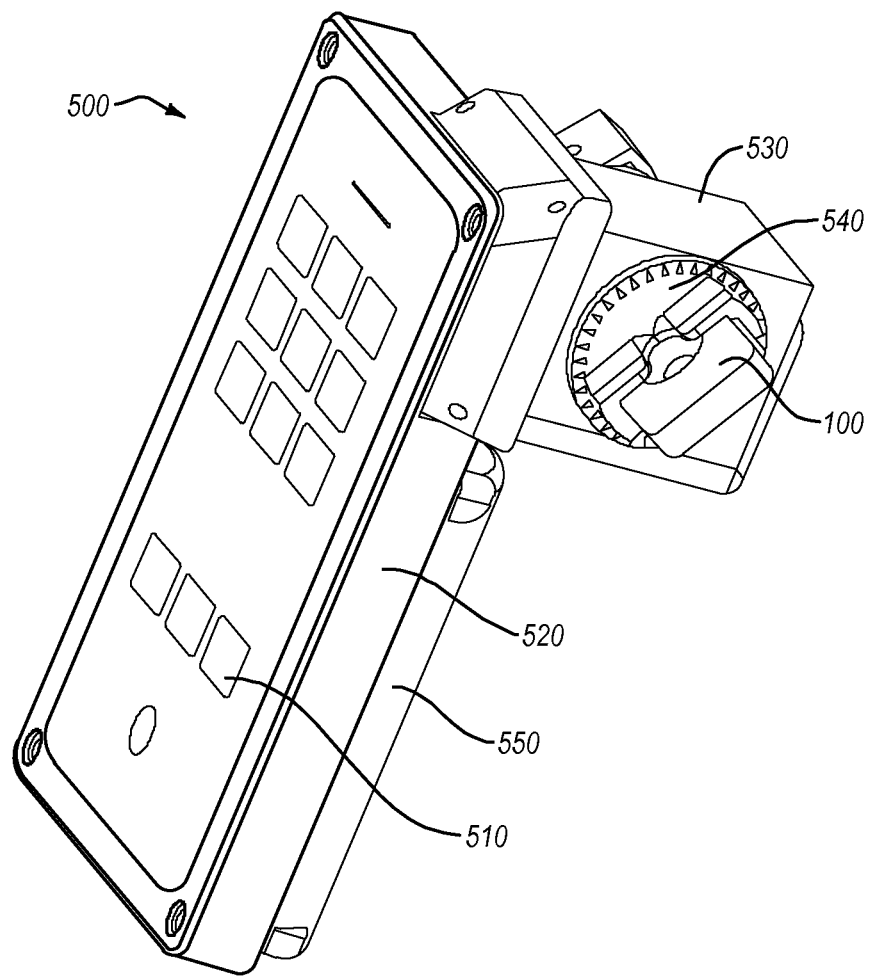
FIG. 3 illustrates a perspective view of a diagnostic testing system that includes a lateral-flow chromatographic immunoassay cassette, a digital camera device, and a holder configured to couple the lateral-flow chromatographic immunoassay cassette to the digital camera device.

Referring now to FIG. 3, a perspective view of a diagnostic testing system 500 is illustrated. The diagnostic testing system 500 includes a lateral-flow chromatographic immunoassay cassette 100, a digital camera device 510, a lower cover 550, and a cassette holder 530 configured to couple the lateral-flow chromatographic immunoassay cassette 100 to the digital camera device 510. The diagnostic testing system 500 also includes a light source (not shown) that can be used to illuminate the lateral-flow chromatographic immunoassay cassette 100 to permit the digital camera device 510 to capture one or more images of the results of an assay in the analysis zone 120 of the lateral-flow chromatographic immunoassay cassette 100.

In one embodiment, the light source (not shown) can include at least one of a camera flash, an autofocus illuminator on a camera, ambient light, sunlight, an LED light, an incandescent lamp, or a gas-discharge lamp. For example, the light source can come from micro-LED lamps that are included in the housing 530. The micro-LEDs can be selected to emit certain wavelengths that are adapted for one or more assay conditions. The micro-LEDs can be powered by drawing electrical power from the battery of digital camera device 510.

In one embodiment, at least one wavelength filter may be interposed between the light source and the lateral-flow chromatographic immunoassay cassette 100. For example, if the assay is a fluorescent assay, then the wavelength filter may be used to yield a specific wavelength of light from the light source to excite fluorescent emission from the assay system. Likewise, certain colored dyes may yield a better signal when excited by selected wavelengths of light.

In one embodiment, the light source may include at least one focusing apparatus (e.g., a collimating lens) for focusing the light source on the lateral-flow chromatographic immunoassay cassette 100. For example, a focusing apparatus may be used to increase the amount of incident light on the analysis zone 120 of the lateral-flow chromatographic immunoassay cassette 100. In another example, a focusing apparatus may be used to focus ambient light or sunlight on the analysis zone 120 of the lateral-flow chromatographic immunoassay cassette 100 in order to allow the digital camera device to capture at least one image of the assay output.

In the illustrated embodiment, the cassette holder 530 includes a device 540 that can allow the angle of the lateral-flow chromatographic immunoassay cassette 100 to be adjusted relative to digital camera device 510 and a light source (not shown). By selectively modifying these angles, the lower detection limit of the assay can be extended, the signal to noise ratio can be improved, etc. In one embodiment, the device 540 can be adjusted manually in order to choose an angle that optimizes detection limit, signal to noise, and the like. In another embodiment, the device 540 can be coupled to a mechanical means, such as a servo motor or a gel-damped spring device that can allow the device 540 to automatically sample a number of angles while the digital camera device 510 captures a number of images of the analysis zone 120 of the lateral-flow chromatographic immunoassay cassette 100.

In the illustrated embodiment, the digital camera device 510 is a camera phone (e.g., an Apple brand iPhone). In other embodiments, the digital camera device 510 can be essentially any camera phone or digital camera. In a preferred embodiment, the digital camera device 510 is a camera phone or digital camera that has an onboard image processing capability and the ability to communicate wirelessly with a database.

Figure 3A:
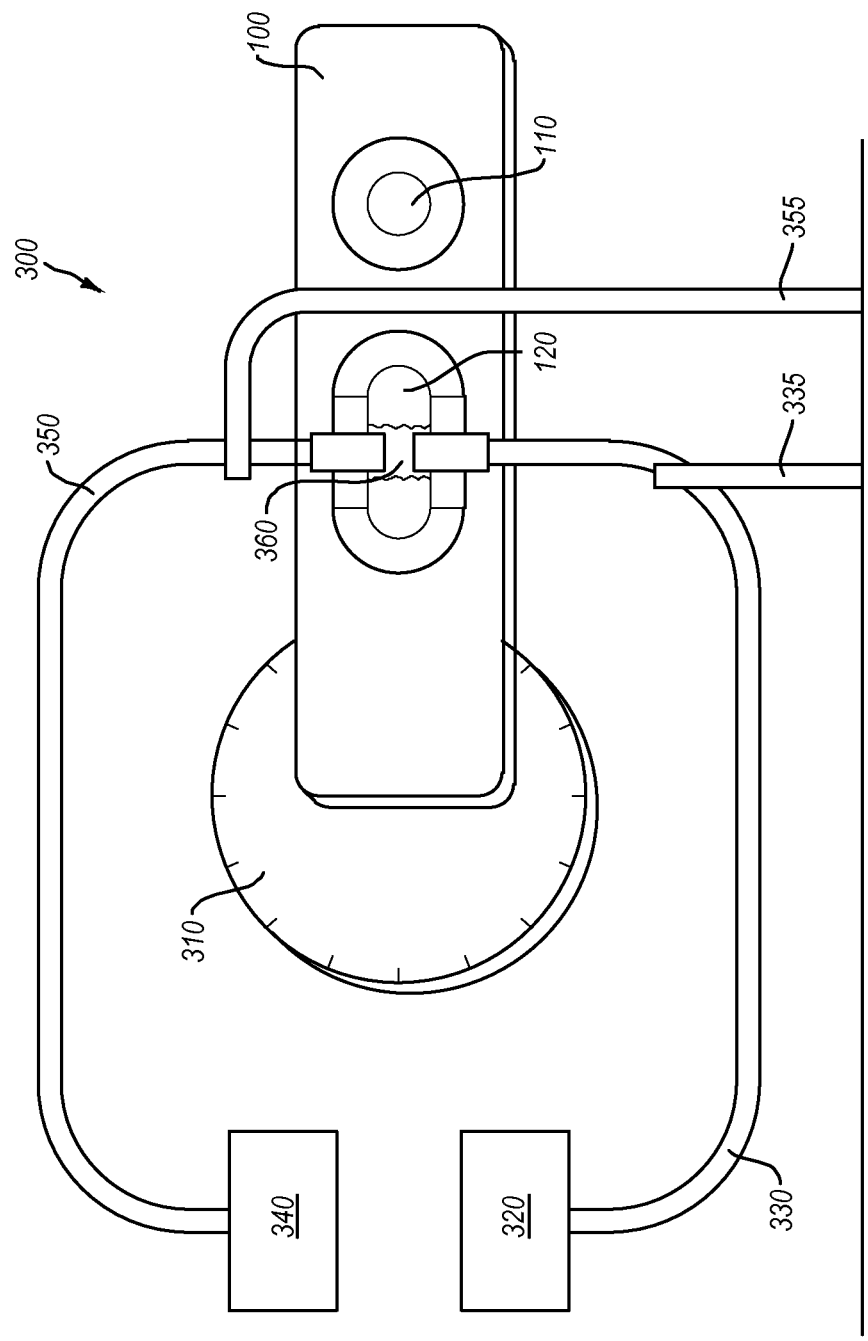
FIG. 3A illustrates a prototype testing device having an illumination source, a miniature spectrophotometer, a pair of optical fibers, and an adjustable variable angle stage holding a lateral-flow chromatographic immunoassay cassette.

FIG. 3A illustrates an apparatus 300 that can be used to test the relationship between illumination angle, detection angle, and fluorescent signal. The apparatus 300 includes an illumination light source 320, a detector device 340, means 330 for transmitting an illuminating light from the illumination source 320 to the lateral-flow chromatographic assay cassette 100, means 350 for transmitting a signal from the lateral-flow chromatographic assay cassette 100 to the detector device 340, and an adjustable variable angle stage 310 configured for adjusting an angle of the lateral-flow chromatographic assay cassette 100 in relation to an illuminating light source and a detector device.

In the illustrated embodiment, the means 330 for transmitting an illuminating light from the illumination source to the lateral-flow chromatographic assay cassette 100 includes an optical fiber. In other embodiment, the means 330 for transmitting an illuminating light from the illumination source to the lateral-flow chromatographic assay cassette 100 may include at least one of a light pipe or one or more lenses. Likewise, in the illustrated embodiment, the means 350 for transmitting a signal from the lateral-flow chromatographic assay cassette 100 to the detector device 340 includes an optical fiber. Other options include at least one of a light pipe or one or more lenses. In the illustrated embodiment, optical fibers 330 and 350 are supported by supports 335 and 355, respectively.

The illuminating light 330 and the and the detector device (or the means 350 for transmitting a signal from the lateral-flow chromatographic assay cassette 100 to the detector device 340) are positioned to illuminate an analysis region 360 of the lateral-flow chromatographic assay cassette 100 and the adjustable variable angle stage 310 is adjustable such that an angle of illumination and an angle of reflection are adjusted in relation to the lateral-flow chromatographic assay cassette 100 so as to optimize an elastic light scattering signal from the lateral-flow chromatographic assay cassette 100.

Figure 3B:
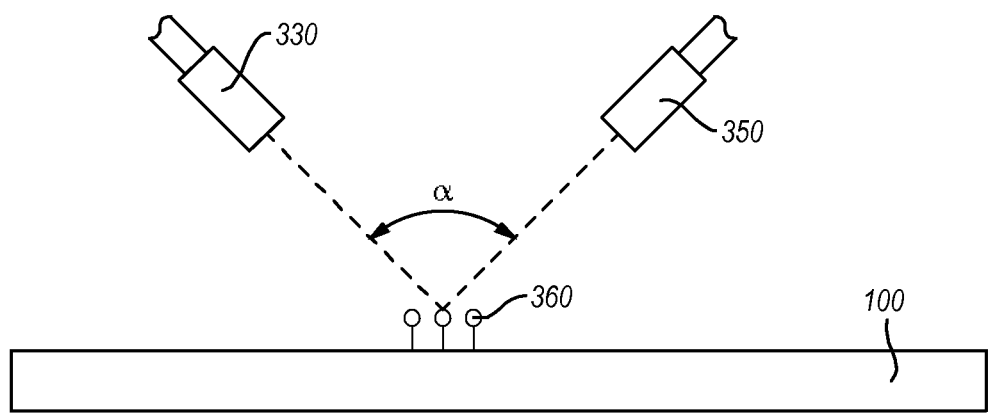
FIG. 3B illustrates a detailed side view of the angle between a lateral-flow chromatographic immunoassay cassette, an illuminating light, and a detector.

FIG. 3B illustrates the principle of adjusting the angle of the illuminating light 330 and the detector device (or the means 350 for transmitting a signal from the lateral-flow chromatographic assay cassette 100 to the detector device 340) relative to the analysis region 360 of the lateral-flow chromatographic assay cassette 100 in greater detail. In the embodiment illustrated in FIG. 3B, there is an angle $\alpha$ between the illuminating light 330 and the detector device (or the means 350 for transmitting a signal from the lateral-flow chromatographic assay cassette 100 to the detector device 340). By adjusting the angle $\alpha$ with the adjustable variable angle stage 310 (FIG. 3A), the elastic light scattering signal from the analysis region 360 of the lateral-flow chromatographic assay cassette 100 can be optimized.

Figure 4:
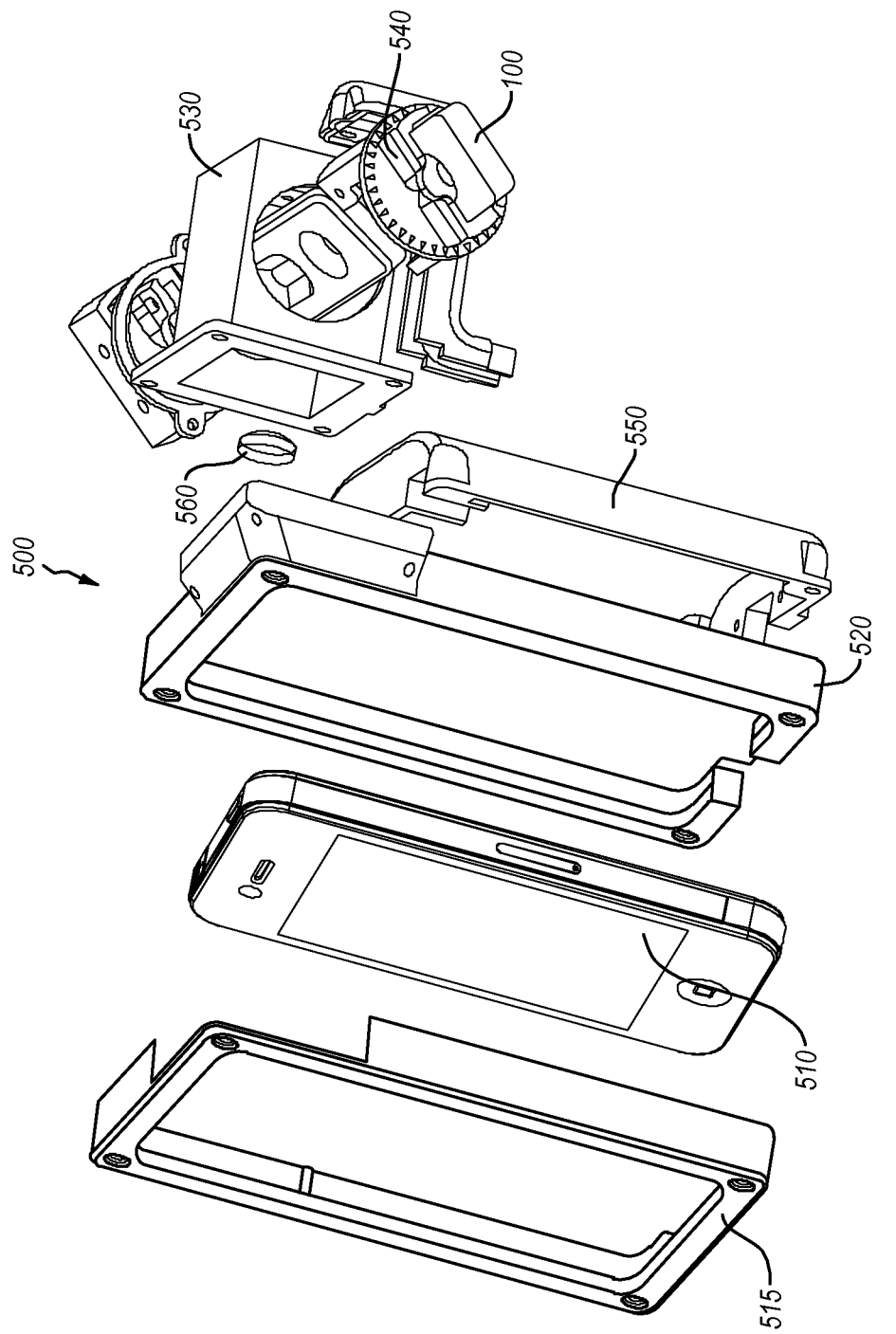
FIG. 4 illustrates an exploded view of the diagnostic testing system that is illustrated in FIG. 3.

Referring now to FIG. 4, an exploded view of the diagnostic testing system 500 of FIG. 3 is illustrated. The diagnostic testing system 500 includes a lateral-flow chromatographic immunoassay cassette 100, a camera phone device 510, a front cover 515, a main cover 520, a collimating lens 560, and a cassette holder 530 configured to couple the lateral-flow chromatographic immunoassay cassette 100 to the camera phone 510. The cassette holder 530 includes an angle adjustment mechanism 540 that allows the user to dynamically adjust the angle between the lateral flow immunoassay cassette 100 and the cell phone 510 to improve the limit of detection or to improve the signal-to-noise ratio.

The purpose of the collimating lens 560 is to bring the focal point of the cell-phone camera 510 (which is usually about 3 feet) to less than 2 centimeters. This allows for a smaller overall package and produces a finer image that prevents the use of convoluting a blurry picture using Fourier transforms in order to produce a usable image that can be analyzed. Furthermore, with a multi-analyte detection assay, the finer image will prevent overlap of the target lines to improve sensitivity and accuracy.

Figure 4A:
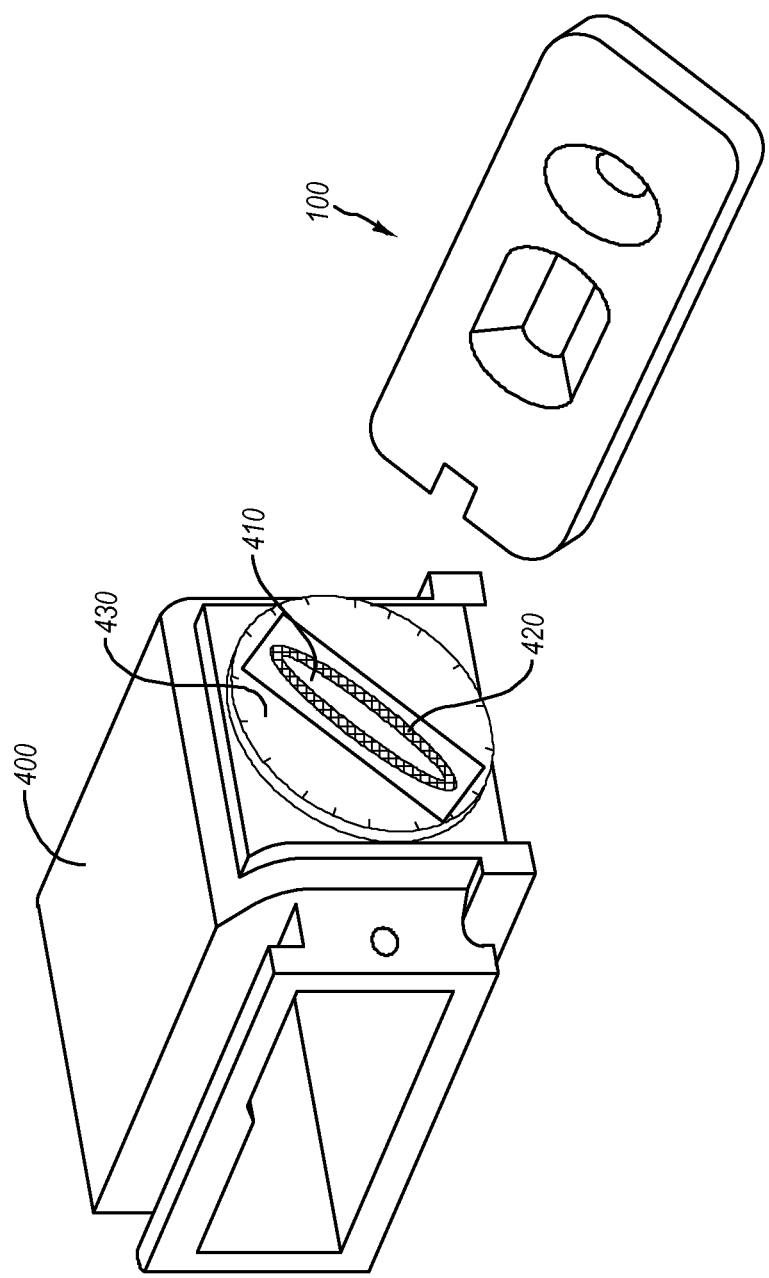
FIG. 4A illustrates a sample holder with an adjustable variable angle stage.

Referring now to FIG. 4A, another embodiment of a sample holder 400 is illustrated. The sample holder 400 may, for example, be coupled directly to a light source and a detector device. The sample holder 410 includes a cassette port 410 that is configured such that a lateral flow immunoassay cassette 100 can be inserted into the sample holder 400. In addition, the cassette port 410 of the sample holder 400 includes an adjustable variable angle device 430 (e.g., a rotatable dial) that allows angle of the cassette 100 to be adjusted relative to a light source and a detector device. By selectively modifying these angles, the lower detection limit of the assay can be extended, the signal to noise ratio can be improved, etc. In one embodiment, the device can be adjusted manually in order to choose an angle that optimizes detection limit, signal to noise, and the like. In another embodiment, the device can be coupled to a mechanical means, such as a servo motor or a gel-damped spring device that can allow the device to automatically sample a number of angles while a detector device collects data from the lateral-flow chromatographic immunoassay cassette 100.

In addition, the cassette port 410 of the sample holder 400 includes a sealing gasket 420 disposed around the cassette port 410 that can seal the cassette port 410 when an assay cassette 100 is inserted therein so that ambient light does not leak into the sample holder 400. For example, if ambient light leaks into the sample holder 400, it could skew results. In addition, the cassette port 410 may include a spring-loaded flap (not shown) or similar means that can seal ambient light out of the sample holder 400 even when no cassette 100 is inserted into the cassette port 410.

Figure 6:
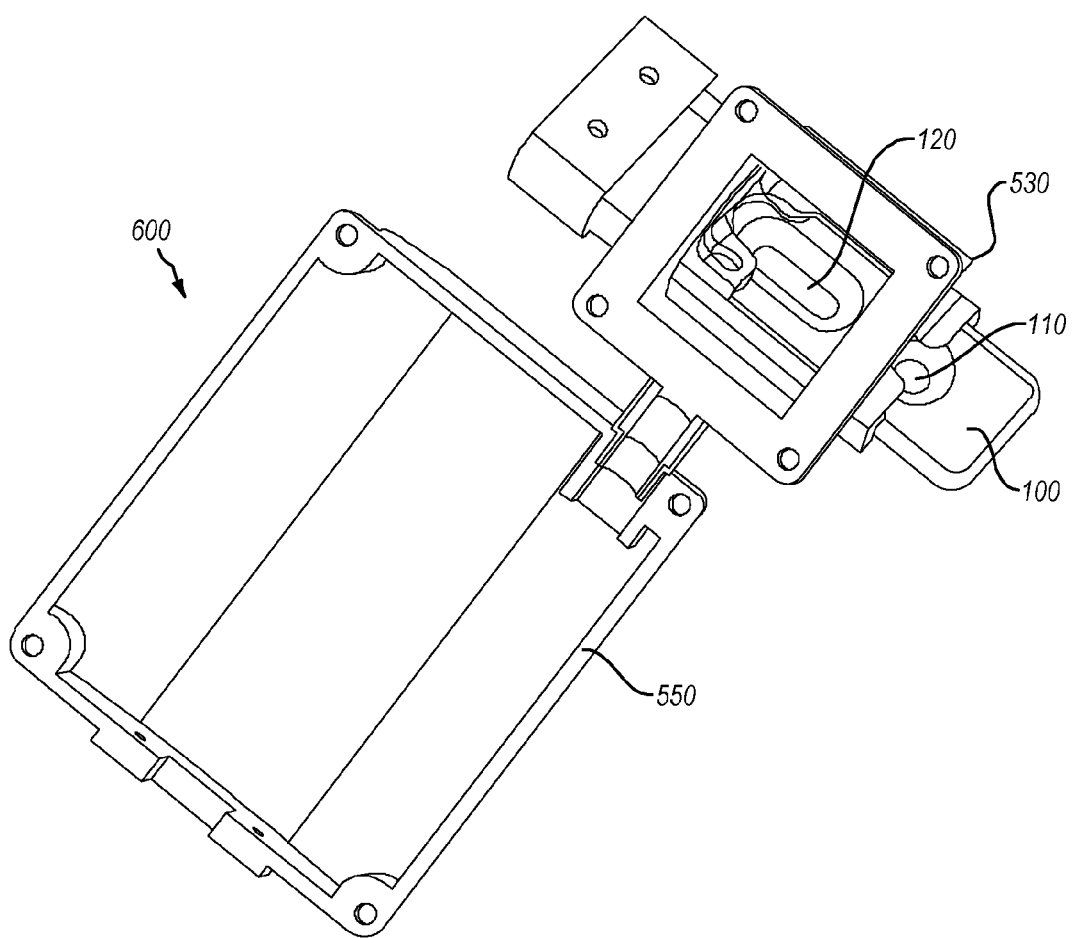
FIG. 6 illustrates a perspective view of the holder and the lateral-flow chromatographic immunoassay cassette illustrated in FIG. 3 with the digital camera device removed.

The inventors have conducted preliminary experiments using the apparatus 300 illustrated in FIG. 3A and a lateral-flow chromatographic immunoassay cassette that is set up to detect thyroid-stimulating hormone ("TSH"). This assay uses ~50 microliters of capillary blood, which is applied at the sample application zone to a nitrocellulose membrane housed in the cassette. At the membrane origin are mobile phase anti-TSH antibodies labeled with colloidal gold. A diluent is deposited on the blood spot and the blood travels the length of the membrane past a test line (which consists of a solid phase capture antibody) and a control line. This is similar to the format of a home pregnancy test. The data shown in FIG. 6 illustrate that by varying the angles of incident and reflected light it is possible to detect the presence of colloidal gold (e.g., signal) at the test line with varying degrees of sensitivity. By optimizing these angles, it may be possible to extend the lower limit of detection of the assay. That is, make it more sensitive.

For example, a standard reference range for TSH for adults is between 0.4 and 5.0 μIU/mL. The therapeutic target range TSH level for patients on treatment ranges between 0.3 to 3.0 μIU/L. TSH levels for children normally start out much higher with age-related reference limits starting from about 1.3 to 19 μIU/mL for normal-term infants at birth, dropping to 0.6-10 μIU/mL at 10 weeks old, 0.4-7.0 μIU/mL at 14 months and gradually dropping during childhood and puberty to adult levels, 0.4-4.0 μIU/mL.

No commercial TSH assay cassette currently on the market is able to provide a visual readout for TSH level below about 0.5 μIU/mL. As such, TSH cassettes cannot currently be used for routine diagnosis of hyperthyroidism. It is believed that by using the devices and methods disclosed herein, that the detection limit can be extended and that TSH cassettes can be used for routine diagnosis of hyperthyroidism and other thyroid related endocrine conditions.

Figure 5:
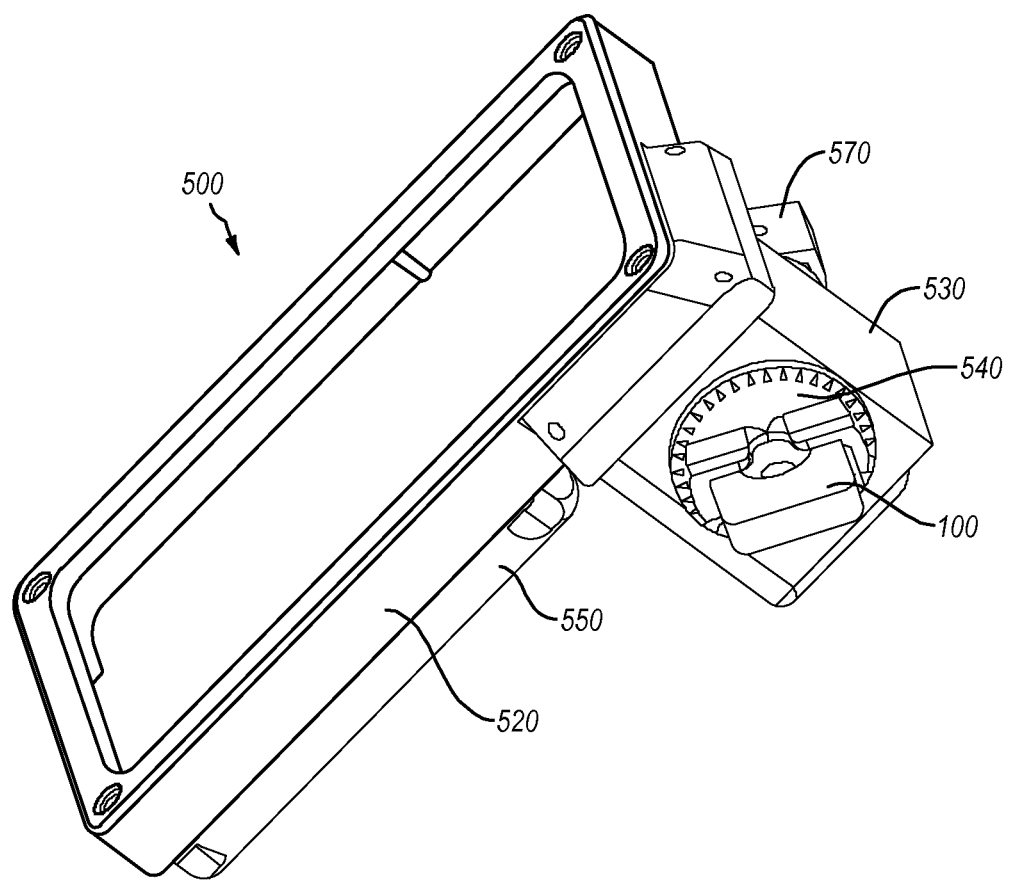
FIG. 5 illustrates a perspective view of the diagnostic testing system illustrated in FIG. 3 with the digital camera device removed.

Referring now to FIG. 5, a perspective view of the diagnostic testing system 500 illustrated in FIG. 3 is illustrated with the digital camera device removed. As can be seen more clearly in FIG. 5, the diagnostic testing system 500 includes a housing 520 that is configured to couple the digital camera device to the holder 530 and, in turn, to the lateral-flow chromatographic immunoassay cassette 100. And while the housing 520 is adapted for fitting an iPhone or a similarly shaped device to the holder 530, the lower cover 550, and the lateral-flow chromatographic immunoassay cassette 100, the housing 520 can be adapted to fit essentially any camera phone, compact digital camera, digital SLR, and the like. FIG. 5 also illustrates an end cap 570 on the lateral-flow chromatographic immunoassay cassette 100.

Figure 5A:
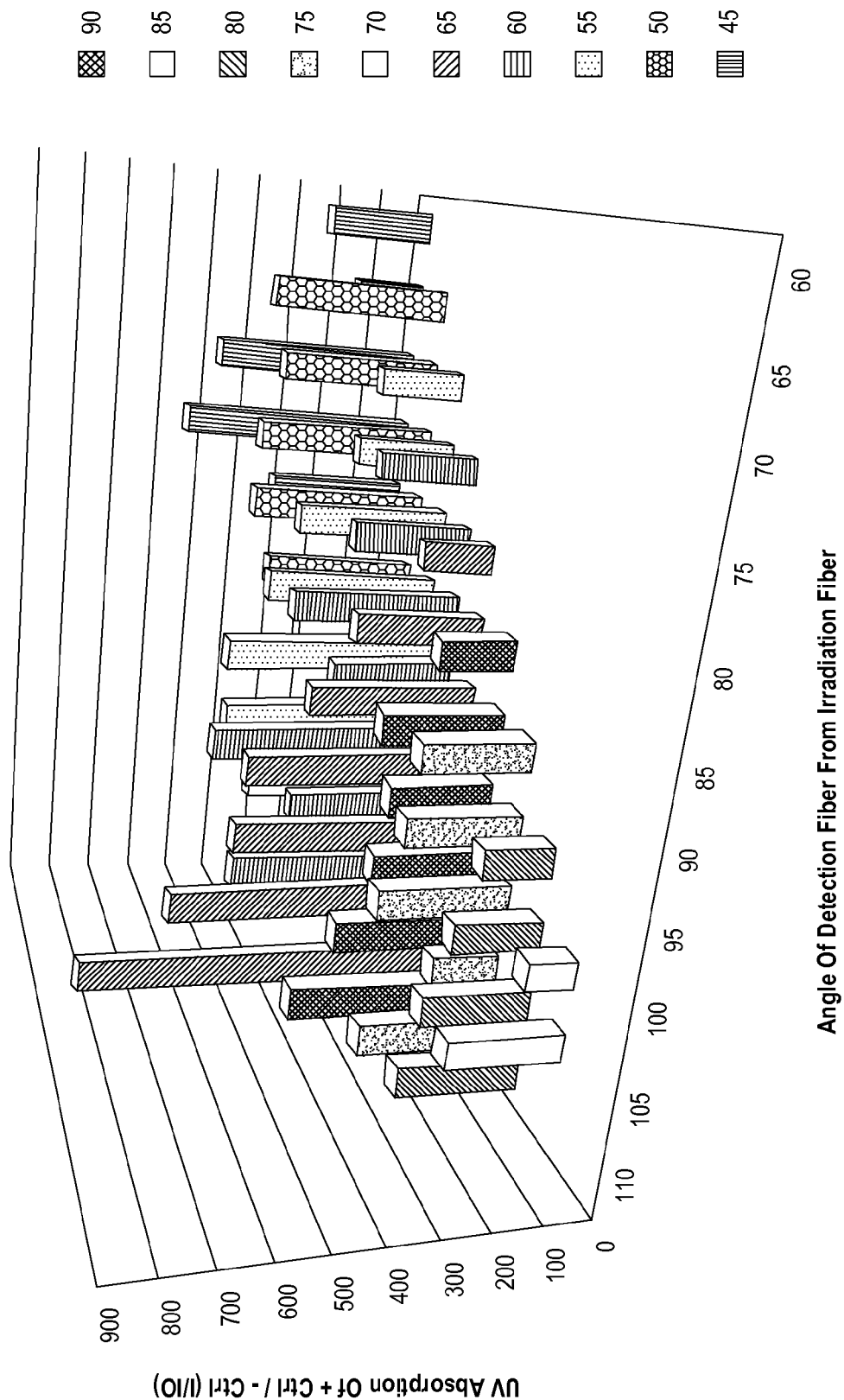
FIG. 5A is a graph illustrating the relationship between the illumination angle on a lateral-flow chromatographic immunoassay cassette and a an elastic light scattering signal obtained from the lateral-flow chromatographic immunoassay cassette at a variety of angles and a variety of loading concentrations using the prototype testing device shown in FIG. 3A.

Referring now to FIG. 5A, a graph depicting the relationship between the illumination angle on a lateral-flow chromatographic immunoassay cassette and a fluorescent signal obtained from the lateral-flow chromatographic immunoassay cassette at a variety of angles and a variety of loading concentrations is illustrated.

Referring now to FIG. 6, a perspective view 600 of the holder 530, the lower cover 550, and the lateral-flow chromatographic immunoassay cassette 100 is illustrated. In the perspective view of FIG. 6, it is possible to see the lateral-flow chromatographic immunoassay cassette 100 as the camera device sees it. As the sample travels from the sample application zone 110 and into the analysis zone 120, the camera device is positioned to capture an image of the result of the assay in the analysis zone 120. Likewise, in the illustrated embodiment in FIG. 6, the camera's flash, which is positioned close to the lens, may be positioned to illuminate the analysis zone 120. As mentioned above, however, the housing 530 may be designed to include another light source or the light source may come from ambient light or sunlight. FIG. 6 also illustrates how the camera's view of the analysis zone 120 could change as the angle of the lateral-flow chromatographic immunoassay cassette 100 with the device 540.

Figure 6A:
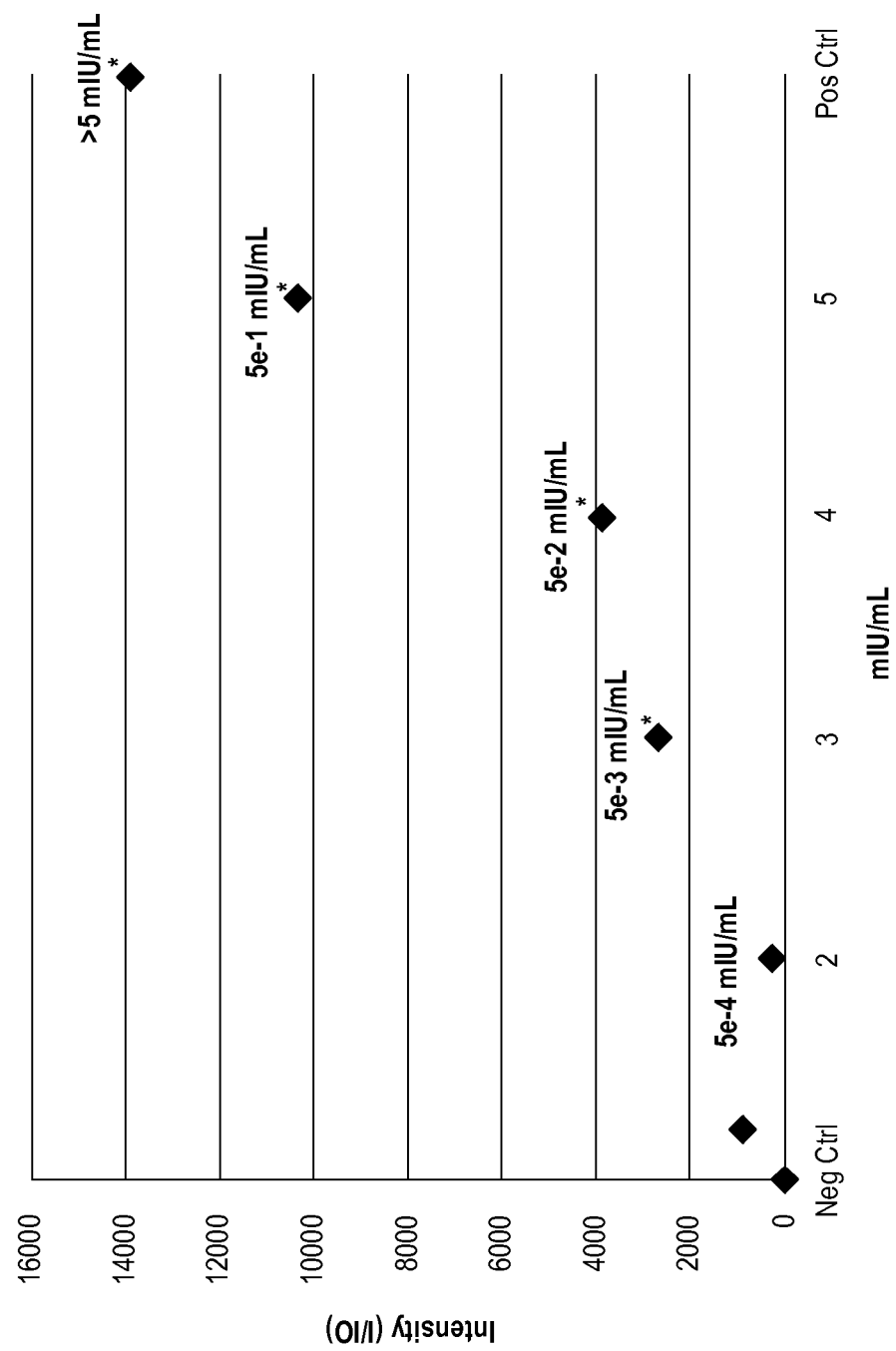
FIG. 6A shows elastic light scattering data for assaying thyroid stimulating hormone dissolved in phosphate buffered saline using the prototype testing device shown in FIG. 3A.

FIG. 6A shows preliminary results for assaying thyroid stimulating hormone dissolved in phosphate buffered saline using the prototype testing device shown in FIG. 3A. The limit of detection is 0.005 mIU/mL.

Figure 7:
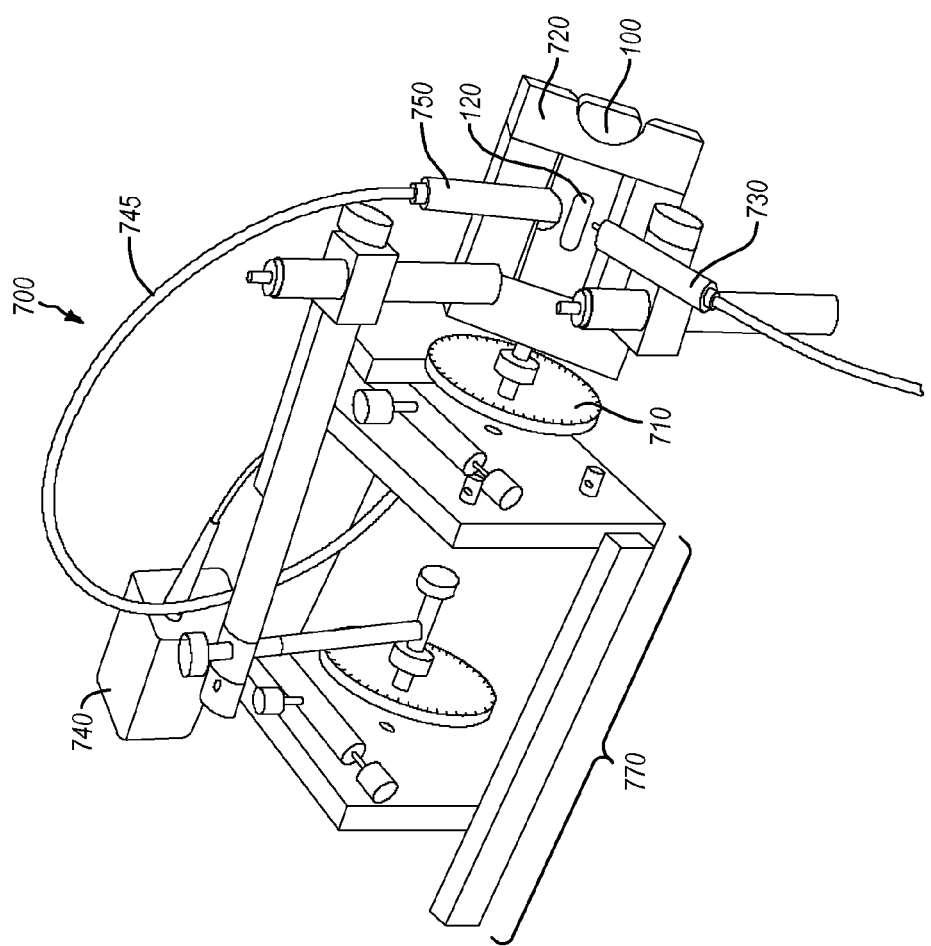
FIG. 7 illustrates a prototype testing device having an illumination source, a miniature spectrophotometer, a pair of optical fibers, and an angularly variable stage holding a lateral-flow chromatographic immunoassay cassette.

FIG. 7 illustrates an apparatus 700 that can be used to test the relationship between illumination angle, detection angle, and fluorescent signal. This is similar to the device that is shown schematically in FIG. 3A. The inventors have conducted preliminary experiments using a lateral-flow chromatographic immunoassay cassette that is set up to detect thyroid-stimulating hormone ("TSH"). This assay uses ~50 microliters of capillary blood, which is applied at the sample application zone to a nitrocellulose membrane housed in the cassette 100. At the membrane origin are mobile phase anti-TSH antibodies labeled with colloidal gold. A diluent is deposited on the blood spot and the blood travels the length of the membrane past a test line (which consists of a solid phase capture antibody) and a control line. This is similar to the format of a home pregnancy test. The data shown in FIGS. 5A and 6A illustrate that by varying the angles of incident and reflected light it is possible to detect the presence of colloidal gold (e.g., signal) at the test line with varying degrees of sensitivity. By optimizing these angles, it may be possible to extend the lower limit of detection of the assay. That is, make it more sensitive.

For example, a standard reference range for TSH for adults is between 0.4 and 5.0 μIU/mL. The therapeutic target range TSH level for patients on treatment ranges between 0.3 to 3.0 μIU/L. TSH levels for children normally start out much higher with age-related reference limits starting from about 1.3 to 19 μIU/mL for normal-term infants at birth, dropping to 0.6-10 μIU/mL at 10 weeks old, 0.4-7.0 μIU/mL at 14 months and gradually dropping during childhood and puberty to adult levels, 0.4-4.0 μIU/mL.

The apparatus 700 includes support means 770, an illumination light source 740, a detector device 730, means 745 for transmitting an illuminating light from the illumination source 740 to a light shining means 750 positioned adjacent to the lateral-flow chromatographic assay cassette 100, means 730 for transmitting a signal from the lateral-flow chromatographic assay cassette 100 to the detector device (not shown), and an adjustable variable angle stage 710/720 configured for adjusting an angle of the lateral-flow chromatographic assay cassette 100 in relation to an illuminating light source and a detector device.

Referring now to FIG. 8, a diagnostic testing system 800 according to another embodiment is illustrated. The diagnostic testing system 800 includes a portable external case 810 that includes essentially all of the components of the diagnostic testing system 800. The diagnostic testing system 800 includes a power switch 804 that is integrated into the case and that can activate the apparatus 800 when the external case 810 is opened. In addition, the diagnostic testing system 800 includes a lateral-flow chromatographic immunoassay cassette 100, a stage 815 holding the lateral-flow chromatographic immunoassay cassette, a light source 806, an angularly adjustable illumination/detection system 820, a power source 806 (e.g., a lithium ion battery pack), and a separate computing device 802 (e.g., a tablet computer or a PDA) that can communicate with the systems either by a wired connection (e.g., via port 808) or wirelessly.

In one embodiment, a tray 816 can be pulled out towards the user, and the lateral flow immunoassay cassette 100 ("LFA") placed inside. A knob 806 that is used to pull the tray 816 out can also be used to move the LFA 100 left and right to position the angularly adjustable illumination/detection system 820 (e.g., a detection fiber or a CCD or similar photodiode) to be able to test different target lines, control, etc. on the LFA 100. The fine adjustment knobs 814 are for positioning the angularly adjustable illumination/detection system 820 to maximize signal intensity. In the illustrated embodiment, a bifurcated cable is shown. In the bifurcated cable, the excitation and detection wavelengths travel through the same fiber. The bifurcated cable can be used for single analyte assays or for multi-analyte detection schemes with multiple capture antibodies and multiple dyes (e.g., quantum dots). In addition to that, there are brackets to place a separate light source fiber or LED light sources if needed.

While the testing in the present application has been conducted with TSH cassettes, it is believed that the same or similar principles can be applied to cassettes adapted for other types of tests.

II. Methods for Detecting at Least One Analyte of Interest in a Sample

In one embodiment, a method for detecting at least one analyte of interest in a sample is disclosed. The method includes (1) providing a lateral-flow chromatographic immunoassay cassette that includes at least one ligand immobilized thereon, wherein the at least one ligand is capable of capturing an analyte of interest on the lateral-flow chromatographic immunoassay cassette (2) applying a liquid sample to the lateral-flow chromatographic immunoassay cassette, wherein the sample includes at least one analyte of interest, (3) coupling the lateral-flow chromatographic assay cassette to a sample holder configured to angle the lateral-flow chromatographic assay cassette in relation to a detector device, and (4) observing the presence of the at least one analyte of interest by elastic light scattering. In one embodiment, the device includes an illumination source, a miniature spectrophotometer, at least one optical fiber capable of transmitting an illuminating light from the illumination source to the lateral-flow chromatographic assay cassette, a collimating lens capable of transmitting a signal from the lateral-flow chromatographic assay cassette to the miniature spectrophotometer, and an adjustable variable angle stage configured for holding the lateral-flow chromatographic assay cassette at an angle greater than or less than zero degrees in relation to the illuminating light and the miniature spectrophotometer, wherein the illuminating light and the and the miniature spectrophotometer are positioned to illuminate at least a portion of the lateral-flow chromatographic assay cassette and optimize an elastic light scattering signal from the lateral-flow chromatographic assay cassette.

In another embodiment, the method includes (1) providing a lateral-flow chromatographic immunoassay cassette that includes at least one ligand immobilized thereon, (2) applying a liquid sample to the lateral-flow chromatographic immunoassay cassette, wherein the sample includes at least one analyte of interest, (3) observing an interaction of the at least one analyte of interest with the at least one ligand immobilized on the lateral-flow chromatographic immunoassay cassette with a device that includes a digital camera device, a light source, and a holder configured to couple the lateral-flow chromatographic immunoassay cassette to the digital camera device in proximity to the light source. The holder is adjustable to adjust the angle of the immunoassay apparatus relative to the light source and the digital camera device to improve at least one of a signal-to-noise ratio or a detection limit for the at least one analyte of interest. The method further includes (4) querying an interpretive algorithm stored in a computer readable format in the digital camera device to convert the observed interaction of the at least one analyte of interest with the at least one ligand visual readout to a numerical value related to the presence or amount of the at least one analyte of interest present in the sample.

In one embodiment, a single immunoassay device may contain multiple types of different antibodies each conjugated with different dyes (e.g., quantum dots) and multiple capture bands each immobilized with different antibodies. A single light source (e.g., an ultraviolet light) illuminates all dyes (e.g., quantum dots) simultaneously, and the detector device (e.g., a digital camera) captures the emitted signals from multiple bands simultaneously.

In one embodiment, analytes of interest assayed on the lateral flow immunoassay cassettes described herein may be detected and quantified by elastic light scattering. The amount of light scattered from a selected region of a lateral flow immunoassay cassette (e.g., a capture band) is highly sensitive to the amount of material in a region illuminated by an incident light. In general, elastic light scattering, coupled with angle optimization, may be as much as 100 times more sensitive than comparable reflectance or fluorescence analysis.

In one embodiment, an ultraviolet light source is positioned at a certain angle to the LFA and the detector (e.g., a detection fiber or a miniature spectrophotometer). In one embodiment, an ultraviolet light source is positioned at a certain angle to the LFA and the detector (e.g., a detection fiber or a cell phone camera) on fiber (eventually the cell phone camera CCD). In one embodiment, a capture band may be queried by taking a reading from the control line of the LFA as a baseline, then a reading from the capture band, and determine the difference in photon intensity. Signal intensity (i.e., the amount of scattered light that is detected) decreases as the concentration of the analyte of interest increases.

In an embodiment that includes a cell phone camera or the like, the camera's CCD will take an image. In this image, both the control and test line will be present. The digital image will then undergo digital signal processing with a selected digital processing algorithm to produce a representative image of the color bands for the control and test simultaneously. The digital processing algorithm will then take an integrative value based on a pre-determined area within each of the bands, and add the intensity values (0-255) of each of these pixels, producing a final intensity count. This will be compared to a standard curved produced, which can be quantified. Internal controls, such as but not limited to, a fluorescent marker to potentially eliminate or reduce variations in the final signal from manufacturing tolerances of the LFA may be used to increase the robustness and reliability of the analysis. Additionally, analysis of the white portion of the LFA may be used as an additional negative control to further improve reproducibility.

In one embodiment, the method may further include mixing the liquid sample with a dye conjugate prior to applying the sample to the lateral-flow chromatographic immunoassay cassette. In one embodiment, the dye conjugate is configured to interact with at least one of the analyte of interest or the ligand to provide a visual readout related to the presence or concentration of the analyte of interest in the sample. In one embodiment, the sample includes at least one control substance and at least one analyte of interest.

In one embodiment, the timing the observing of the interaction of the at least one analyte of interest with the at least one ligand immobilized on the lateral-flow chromatographic immunoassay cassette by observing the at least one control substance. For example, the TSH assay is read 10 minutes after the diluent is applied. By monitoring the position of the wave front or the appearance of the control line, we can eliminate the need to manually time the test. Likewise, by observing the timing of the appearance of a control, the most favorable time for reading the assay can be identified. These could include monitoring the movement of the mobile phase, monitoring the movement of the control substance, timing the movement of the mobile phase, taking sequential images of the test result, detecting when buffer is added, detecting when liquid has traveled the length of the membrane, and combinations thereof.

The positive control substance can also be used for calibrating the test. This device is intended to provide quantitative results. To do this requires calibrating the test. In one embodiment, the test may be calibrated by adding a quantity (e.g., a known quantity) of a positive control substance (e.g., a solution of fluorescent particles) to the diluent. The light source will generate light at wavelengths to optimize the detection of the test line and to illuminate the positive control substance. The digital camera device can detect the amount of light that is scattered or emitted by the positive control substance and use this information to normalize the scattering or emission from the analyte of interest. In addition to providing calibration data, the positive control substance can be used to time the reaction and to demonstrate that the assay functioned correctly. In addition, the test can be further calibrated or quantified by including a color scale that is printed on the body of the assay cassette adjacent to the cassette window. The color scale could also serve as an addition means for calibrating the test result.

In one embodiment, an interpretive algorithm may be queried for interpretation of the elastic light scattering signal. The interpretive algorithm may include one or more computer storage media having stored thereon computer executable instructions that, when executed by one or more processors, implement a method for interpreting the numerical value related to the presence or amount of the at least one analyte present in the sample. In one embodiment, the computer implemented method includes (1) receiving a user initiated request to convert the visual signal readout of the immunoassay apparatus to a numerical value, (2) in response to the request, an act of identifying at least one elastic light scattering signal of the immunoassay apparatus, (3) capturing at least one elastic light scattering signal from the immunoassay apparatus, (4) converting the one elastic light scattering signal to at least one numerical value proportional at least one of an intensity or density of the elastic light scattering signal, and (5) using the at least one numerical value to determine an amount or concentration of at least one analyte present in the sample. This numerical value can then be displayed on a screen located on the detector device and/or stored, interpreted, or sent to a database.

In one embodiment, the interpretive algorithm queried in step (4) of the above described method may include one or more computer storage media having stored thereon computer executable instructions that, when executed by one or more processors of the detector device, implement a method for interpreting the numerical value related to the presence or amount of the at least one analyte present in the sample. In one embodiment, the computer implemented method includes (1) receiving a user initiated request to convert the visual signal readout of the immunoassay apparatus to a numerical value, (2) in response to the request, an act of identifying at least one visual signal readout of the immunoassay apparatus, (3) capturing at least one digital photographic image of the at least one visual signal readout of the immunoassay apparatus, (4) converting the at least digital photographic image to at least one numerical value proportional to at least one of an intensity, a density, or a number of pixels in the at least one digital photographic image of the at least one visual signal readout of the immunoassay apparatus, and (5) using the at least one numerical value to determine an amount or concentration of at least one analyte present in the sample. This numerical value can then be displayed on a screen located on the detector device and/or stored, interpreted, or sent to a database.

In one embodiment, the computer implemented method may further include at least one of: (1) communicating with an electronic medical records system via a wireless communication channel, (2) uploading the amount or concentration of the at least one analyte present in the sample to the electronic medical records system, or (3) querying a decision support algorithm, wherein the decision support algorithm uses the at least one numerical value to support a diagnosis of at least one condition in a subject and to suggest a course of treatment.

Embodiments of the present disclosure may comprise or utilize special purpose or general-purpose computing devices that include computer hardware, such as, for example, one or more processors and system memory, as discussed in greater detail below. Embodiments within the scope of the present invention also include physical and other computer-readable and recordable type media for carrying or storing computer-executable instructions and/or data structures. Such computer-readable recordable media can be any available media that can be accessed by a general purpose or special purpose computer system. Computer-readable media that store computer-executable instructions according to the invention are recordable-type storage media or other physical computer storage media (devices) that are distinguished from mere transitory carrier waves.

Computer-readable media that carry computer-executable instructions are transmission media. Thus, by way of example, and not limitation, embodiments of the invention can comprise at least two distinctly different kinds of computer-readable recordable media: computer storage media (devices) and transmission media.

Computer storage media (devices) includes RAM, ROM, EEPROM, CD-ROM or other optical disk storage, magnetic disk storage or other magnetic storage devices, or any other medium which can be used to store desired program code means in the form of computer-executable instructions or data structures and which can be accessed by a general purpose or special purpose computer and which are recorded on one or more recordable type medium (device).

A "network" is defined as one or more data links or communication channels that enable the transport of electronic data between computer systems and/or modules and/or other electronic devices. When information is transferred or provided over a network or another communications connection or channel (either hardwired, wireless, or a combination of hardwired or wireless) to a computer, the computer properly views the connection as a transmission medium. Transmissions media can include a network and/or data links which can be used to carry or desired program code means in the form of computer-executable instructions or data structures and which can be accessed by a general purpose or special purpose computer. Combinations of the above should also be included within the scope of computer-readable media.

Further, upon reaching various computer system components, program code means in the form of computer-executable instructions or data structures can be transferred automatically from transmission media to computer storage media (devices) (or vice versa). For example, computer-executable instructions or data structures received over a network or data link can be buffered in RAM within a network interface module (e.g., a "NIC"), and then eventually transferred to computer system RAM and/or to less volatile computer storage media (devices) at a computer system. Thus, it should be understood that computer storage media (devices) can be included in computer system components that also (or even primarily) utilize transmission media.

Computer-executable instructions comprise, for example, instructions and data which, when executed at a processor, cause a general purpose computer, special purpose computer, or special purpose processing device to perform a certain function or group of functions. The computer executable instructions may be, for example, binaries, intermediate format instructions such as assembly language, or even source code. Although the subject matter has been described in language specific to structural features and/or methodological acts, it is to be understood that the subject matter defined in the appended claims is not necessarily limited to the described features or acts described herein. Rather, the described features and acts are disclosed as example forms of implementing the claims.

Those skilled in the art will appreciate that the invention may be practiced in network computing environments with many types of computer system configurations, including, personal computers, desktop computers, laptop/notebook computers, message processors, hand-held devices, multiprocessor systems, microprocessor-based or programmable consumer electronics, network PCs, minicomputers, mainframe computers, tablets, mobile telephones, PDAs, pagers, routers, switches, and the like. The invention may also be practiced in distributed system environments where local and remote computer systems, which are linked (either by hardwired data links, wireless data links, or by a combination of hardwired and wireless data links) through a network, both perform tasks. In a distributed system environment, program modules may be located in both local and remote memory storage devices.

In particular, one or more embodiments of the invention may be practiced with mobile consumer computing devices. Mobile consumer computing devices or more simply, mobile consumer devices, can be any of a broad range of computing devices designed or optimized for portability and for personal use. Mobile consumer devices can take a variety of forms, ranging from more traditional notebook and netbook computers to an emerging and rapidly growing market of handheld devices, including smart phones (e.g., the APPLE IPHONE, ANDROID phones, WINDOWS phones, SYMBIAN phones), tablet computers (e.g., the APPLE IPAD, ANDROID tablets), gaming devices (e.g., NINTENDO or PLAYSTATION portable gaming devices, the APPLE IPOD), multimedia devices (e.g., the APPLE IPOD), and combinations thereof. Many of these devices can enable rich user-interactivity by including combinations of output, input, and other sensory devices, such as touch- or pressure-sensitive displays (using capacitive or resistive technologies, for example), still and video cameras, Global Positioning System (GPS) receivers, magnetic compasses, gyroscopes, accelerometers, light sensors, proximity sensors, microphones, speakers, etc. These devices can also comprise a variety of communications devices, such as combinations of cellular modems (e.g., Global System for Mobile Communications (GSM), Code division multiple access (CDMA)), Wireless Fidelity (Wi-Fi) radios, Bluetooth radios, Near Field Communication (NFC) devices, etc. Many mobile consumer devices are expandable, such that a user can add new hardware and functionality not present during manufacture of the device. It will be appreciated that as the market for mobile consumer devices expands and develops, the functionality of these devices will also expand to utilize new and improved user-interaction devices and communications devices. The embodiments described herein are expansive and can also utilize any future developments in the field of mobile consumer devices.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. A system, comprising:
   a lateral flow chromatographic assay cassette including a sample application zone in fluid communication with a test zone via a fluid transport matrix, the test zone having a calibration line and a test line;
   a light source to illuminate the lateral-flow chromatographic assay cassette with at least one wavelength of light selected to yield a detectable signal from the calibration line and the test line, wherein the detectable signal is one or more of fluorescence, reflectance, diffuse scattering, elastic light scattering, or chemiluminescence, chemifluorescence, wherein the light source includes at least one of a camera flash, an autofocus illuminator, ambient light, sunlight, an LED light, an incandescent lamp, or a gas-discharge lamp;
   a detector device for data collection and data analysis, the detector device comprising a handheld computing device that includes a camera, wherein the handheld computing device is selected from the group consisting of a handheld digital camera, a camera phone, a smartphone, and a tablet computer;

a sample holder coupled to the handheld computing device and configured to position the lateral-flow chromatographic assay cassette in relation to the camera and the light source to control focal length from the camera to the lateral-flow chromatographic assay cassette and to control illumination of the lateral-flow chromatographic assay cassette by the light source, wherein the sample holder includes a slot sized for insertion of the lateral-flow chromatographic assay cassette into the sample holder and a angularly adjustable stage configured for adjustment detector device; and a collimating lens positioned between the camera and the lateral-flow chromatographic assay cassette such that the camera can image the lateral-flow chromatographic assay cassette in a single image.

2. The system of claim 1, wherein the detector device further comprises one or more computer readable media having stored thereon computer-executable instructions that are executable by the one or more processors to reprogram the handheld computing device with an algorithm that uses the handheld computing device to process the detectable signal from the lateral-flow chromatographic assay cassette and convert the detectable signal to a numerical value for quantification of the amount of at least one analyte in the sample.

3. The system of claim 1, wherein the sample holder includes an electrical connector configured to draw power from the detector device to power the light source.

4. The system of claim 1, wherein the camera includes at least one of a CCD or a CMOS chip.

5. The system of claim 1, wherein the light source is one of a flash or autofocus illuminator included on the camera.

6. The system of claim 1, wherein at least one filter is interposed between the light source and the assay apparatus.

7. The system of claim 1, wherein the light source is an LED light.

8. The system of claim 1, wherein the light source is configured to yield at least one wavelength of light selected to convert the detectable signal of the lateral flow assay cassette to a fluorescent or chemiluminescent emission signal.

9. The system of claim 1, further comprising a focusing apparatus for increasing the amount of incident light on the test zone of the lateral-flow chromatographic assay cassette.

10. The system of claim 1, wherein the lateral-flow chromatographic assay cassette comprises:

a base;

an absorbent strip positioned above the base including a wicking material, wherein the strip includes a distal end and a proximal end; and the sample application zone positioned between the distal end and the proximal end, wherein a liquid sample applied to the sample application zone diffuses through the absorbent strip from the distal end to the proximal end, and wherein an analyte of interest, if present in the sample, interacts with at least a first antibody immobilized in the absorbent strip to yield the detectable signal.

11. The system of claim 1, wherein the sample holder is configured to adjust the angle of the lateral-flow chromatographic assay cassette relative to the light source and the detector device to improve at least one of a signal-to-noise ratio or a detection limit.

12. The system of claim 1, wherein the holder includes a device for automatically sampling a number of angles of the lateral-flow chromatographic assay cassette relative to the light source and the detector device to improve at least one of a signal-to-noise ratio or a detection limit.

13. The system of claim 1, further comprising a light pipe or optical fiber for transmitting an illuminating light from the light source to the assay apparatus.

* * * * *